(12) United States Patent
Lu et al.

(10) Patent No.: US 9,234,227 B2
(45) Date of Patent: Jan. 12, 2016

(54) RECOMBINANT PHAGE AND METHODS

(71) Applicant: Sample6 Technologies, Inc., Boston, MA (US)

(72) Inventors: Timothy Kuan Ta Lu, Charlestown, MA (US); Michael Sandor Koeris, Natick, MA (US); Brett Smith Chevalier, Malden, MA (US); Jason Wyatt Holder, Somerville, MA (US); Gregory John McKenzie, Arlington, MA (US); Daniel Robert Brownell, Arlington, MA (US)

(73) Assignee: Sample6 Technologies, Inc., Cambridge, MA (US)

( * ) Notice: Subject to any disclaimer, the term of this patent is extended or adjusted under 35 U.S.C. 154(b) by 0 days.

(21) Appl. No.: 13/627,060

(22) Filed: Sep. 26, 2012

(65) Prior Publication Data
US 2013/0122549 A1    May 16, 2013

Related U.S. Application Data

(60) Provisional application No. 61/539,454, filed on Sep. 26, 2011, provisional application No. 61/549,743, filed on Oct. 20, 2011, provisional application No. 61/642,691, filed on May 4, 2012.

(51) Int. Cl.
| | |
|---|---|
| *C12N 15/00* | (2006.01) |
| *C12P 19/34* | (2006.01) |
| *C12N 15/10* | (2006.01) |
| *C12N 15/81* | (2006.01) |
| *C12N 15/86* | (2006.01) |

(52) U.S. Cl.
CPC ............... *C12P 19/34* (2013.01); *C12N 15/10* (2013.01); *C12N 15/81* (2013.01); *C12N 15/86* (2013.01); *C12N 2795/10143* (2013.01); *C12N 2795/10243* (2013.01); *C12N 2800/206* (2013.01)

(58) Field of Classification Search
None
See application file for complete search history.

(56) References Cited

U.S. PATENT DOCUMENTS

| | | | | |
|---|---|---|---|---|
| 6,033,898 | A * | 3/2000 | Sarthy et al. | 435/254.21 |
| 2010/0015595 | A1 | 1/2010 | Siegel | |
| 2011/0053272 | A1* | 3/2011 | Benders et al. | 435/455 |

OTHER PUBLICATIONS

Ketner, Gary, et al., Proc. Natl. Acad. Sci., USA, vol. 91, pp. 6186-6190 (1994).

Kouprina, Natalay, et al., Nature Reviews Genetics, vol. 7, pp. 805-812 (2006).
International Search Report, Application No. PCT/US12/57214, mailed Jan. 24, 2013.
Written Opinion of the International Searching Authority, Application No. PCT/US12/57214, mailed Jan. 24, 2013.
Fernando Almazan, "Engineering the largest RNA virus genome as an infectious bacterial artificial chromosome," PNAS, vol. 97, No. 10 pp. 5516-5521 (2000).
Arban Domi, "Cloning the vaccinia virus genome as a bacterial artificial chromosome in *Escherichia coli* and recovery of infectious virus in mammalian cells," PNAS, vol. 99, No. 10, pp. 12415-12420 (2002).
Geneart® High-Order Genetic Assembly System User Manual, Invitrogen (2010).
Paul R. Jaschke, "A fully decompressed synthetic bacteriophage øX174 genome assembled and archived in yeast," Virology, vol. 434, pp. 278-284 (2012).
Gary Ketner, "Efficient manipulation of the human adenovirus genome as an infectious yeast artificial chromosome clone," PNAS vol. 91, pp. 6186-6190 (1994).
Martin J. Loessner "Construction of Luciferase Reporter Bacteriophage A511::luxAB for Rapid and Sensitive Detection of Viable Listeria Cells," Applied and Environmental Microbiology, vol. 62, No. 4, pp. 1133-1140 (1996).
Lansha Peng, "Next-Generation DNA Assembly Tools," vol. 30, No. 18, 2010.
Christopher K. Raymond, "Linker-Mediated Recombinational Subcloning of Large DNA Fragments Using Yeast," Genome Research, vol. 12, pp. 190-197 (2002).
James A. Sawitzke, "Recombineering: In Vivo Genetic Engineering in *E. coli, S. enterica*, and Beyond," Methods in Enzymology, vol. 421, pp. 171-199 (2007).
Shyman K. Sharan, "Recombineering: A Homologous Recombination-Based Method of Genetic Engineering," Nat. Protocol., vol. 4, No. 2, pp. 206-223 (2010).
Mila Vrancic, "Mammalian Genome Recombineering: Yeast, Still a Helper Microorganism of Choice?," Food Technol. Biotechnol., vol. 46, No. 3, pp. 237-251 (2008).

\* cited by examiner

*Primary Examiner* — Michele K Joike
*Assistant Examiner* — Mindy G Brown
(74) *Attorney, Agent, or Firm* — Cooley, LLP; Ivor Elrifi; Matthew Pavao

(57) ABSTRACT

This disclosure provided methods of cloning a phage genome. Also provided are methods of making a recombinant phage genome. In some embodiments the phage genome is engineered to comprise a heterologous nucleic acid sequence, for example a sequence comprising an open reading frame. In some embodiments the phage genome is cloned in a yeast artificial chromosome. Recombinant phage genomes and recombinant phage are also provided. In some embodiments the methods are high throughput methods such as methods of making a plurality of recombinant phage genomes or recombinant phage. Collections of recombinant phage genomes and recombinant phage are also provided.

8 Claims, 5 Drawing Sheets

RECOMBINANT PHAGE AND METHODS

REFERENCE TO RELATED APPLICATIONS

This application claims priority to U.S. Provisional Patent Application No. 61/539,454, filed Sep. 26, 2011; U.S. Provisional Patent Application No. 61/549,743, filed Oct. 20, 2011; and U.S. Provisional Patent Application No. 61/642,691, filed May 4, 2012. The entire contents of each of those applications are hereby incorporated herein by reference.

SEQUENCE LISTING

The instant application contains a Sequence Listing which has been submitted in ASCII format via EFS-Web and is hereby incorporated by reference in its entirety. Said ASCII copy, created on Nov. 14, 2012, is named 1211USNP.txt and is 12,065 bytes in size.

INTRODUCTION

Model phage have been engineered using molecular biology techniques to deliver heterologous protein products to bacterial cells. For example, phage have been engineered to deliver enzymes to biofilms to digest the extracellular matrix and destroy the biofilm. (E.g., U.S. Patent Application Publication No. 2009/0155215.) Phage have also been engineered to express protein products that can be visualized in order to detect the presence of a particular type of bacterial cell that is susceptible to infection by the phage. (E.g., "Construction of Luciferase Reporter Bacteriophage A511::luxAB for Rapid and Sensitive Detection of Viable *Listeria* Cells," M. J. Loessner et. al., *Applied and Environmental Microbiology*, Vol. 62, No. 4, pp. 1133-40 (1996).) The natural host range of the phage engineered to date is a limitation, however, and those phage don't infect many relevant bacteria and biofilms.

Methods of engineering additional phage, with more varied host range, will contribute to expansion of the use of phage engineering technology. High throughput methods of creating variations in phage genomes and engineered phage genomes will also contribute to identification of phage with varied properties that are useful for diagnostic and therapeutic purposes. To date such methods have in general been lacking, however, and therefore additional methods of engineering phage will be useful.

Engineering diverse phage is generally made more difficult by the properties of phage genomes. For example, phage genomes have relatively few restriction sites and are heavily modified, making use of traditional cloning techniques with phage challenging. Phages also have compact genomes with very little non-coding DNA, which can make it challenging to find sites within the genome that are compatible with traditional engineering.

One approach for cloning phage DNA relies on isolating phage DNA, cutting the DNA with restriction enzymes, and transforming the DNA back into the host for recombination into viable phage. A second approach is to clone a part of a phage genome in a plasmid, engineer in a heterologous sequence and transfer that heterologous sequence into a relevant host strain. These cells can be infected with wild-type phages, allowing for homologous recombination between the phage and the heterologous sequence. Screening for recombinant phages will reveal the engineered phages. These techniques have succeeded in isolated instances. (E.g., "Construction of Luciferase Reporter Bacteriophage A511::luxAB for Rapid and Sensitive Detection of Viable *Listeria* Cells," M. J. Loessner et. al., *Applied and Environmental Microbiology*, Vol. 62, No. 4, pp. 1133-40 (1996).) However, the process must be completed before any engineered phage can be tested. The whole process must be repeated, end-to-end, for any new insertion site within a particular phage. If a site is not viable, the entire process must be repeated for the next insertion site.

The inventors sought to develop more useful methods of cloning phage DNA and creating genetically engineered phage by using transformation associated recombination techniques to clone whole phage genomes. This technique is described in N., Larionov, V., October 2006. TAR cloning: insights into gene function, long-range haplotypes and genome structure and evolution 7 (10), 805-812. In experiments with Lambda phage, no more than 83% of the total Lambda genome was verified. With this result, the process was deemed unsuitable for many uses.

The inventors have since surprisingly found that phage genomes are not lethal in yeast cells and thus that phage can be cloned into suitable vectors and propagated in yeast. The inventors have exploited this finding to develop recombinant vectors comprising phage genomes. In some embodiments the phage genome is engineered to comprise a heterologous nucleic acid sequence, for example a sequence comprising an open reading frame. The vectors are useful, for example, to make genetically modified phage. Also provided are methods of cloning a phage genome. Also provided are methods of making a recombinant phage genome. In some embodiments the phage genome is engineered to comprise a heterologous nucleic acid sequence, for example a sequence comprising an open reading frame. Recombinant phage genomes and recombinant phage are also provided. In some embodiments the methods are high throughput methods such as methods of making a plurality of recombinant phage genomes or recombinant phage. Collections of recombinant phage genomes and recombinant phage are also provided. These and other aspects of the disclosure are described more fully herein.

The methods and recombinant vectors, phage genomes, and phage provided herein are a major advancement over current phage engineering technologies which rely on in vitro strategies, which are generally inefficient and challenging to scale up, or on engineering phages within bacteria, which is generally problematic due to toxicity of phages to bacteria and the difficulty in maintaining the stability of large engineered genomes.

SUMMARY

In a first aspect, methods of making a cloned phage genome are provided. In some embodiments the methods comprise providing a vector, inserting a starting phage genome into the vector to provide a recombinant vector, and propagating the recombinant vector in a vector host cell that is not a phage host cell to thereby provide the cloned phage genome. In some embodiments of the methods the recombinant vector comprising a starting phage genome is made by a method comprising co-transforming the starting phage genome and the vector into a plurality of vector host cells, under conditions that allow insertion of the starting phage genome into the vector, and selecting a vector host cell comprising the recombinant vector as a result of insertion of the starting phage genome into the vector. In some embodiments of the methods the recombinant vector comprising a starting phage genome is made by a method comprising transforming the starting phage genome into a plurality of vector host cells comprising the vector, under conditions that allow insertion of the starting phage genome into the vector, and selecting a vector host cell comprising the recombinant vector as a result of insertion of the starting phage genome into the vector. In some embodiments the methods further comprise isolating the recombinant vector. In some embodiments the methods further comprise removing the cloned phage genome from the recombinant vector. In some embodiments the cloned phage genome is removed from the recombinant vector by a method comprising transforming the recombinant vector comprising the cloned phage genome into competent phage host cells, and culturing the phage host cells under conditions sufficient for production of phage particles comprising the cloned phage genome. In some embodiments the methods further comprise isolating the cloned phage genome. In some embodiments the vector is a yeast artificial chromosome and the vector host cell is a yeast cell.

In a second aspect methods of making a recombinant phage genome are also provided. In some embodiments the methods comprise providing vector host cells comprising a recombinant vector comprising a cloned phage genome, inserting a heterologous nucleic acid sequence into the starting phage genome to provide a recombinant phage genome, and selecting vector host cells comprising the recombinant vector comprising the recombinant phage genome to thereby provide the cloned phage genome. In some embodiments of the methods the recombinant vector comprising a cloned phage genome is made by a method comprising providing a vector, inserting a starting phage genome into the vector to provide the recombinant vector, and propagating the recombinant vector in a vector host cell that is not a phage host cell to thereby provide the recombinant vector comprising a cloned phage genome. In some embodiments of the methods the recombinant vector comprising a starting phage genome is made by a method comprising co-transforming the starting phage genome and the vector into a plurality of vector host cells, under conditions that allow insertion of the starting phage genome into the vector, and selecting a vector host cell comprising the recombinant vector as a result of insertion of the starting phage genome into the vector. In some embodiments of the methods the recombinant vector comprising a starting phage genome is made by a method comprising transforming the starting phage genome into a plurality of vector host cells comprising the vector, under conditions that allow insertion of the starting phage genome into the vector, and selecting a vector host cell comprising the recombinant vector as a result of insertion of the starting phage genome into the vector. In some embodiments the methods further comprise isolating the recombinant vector comprising the recombinant phage genome. In some embodiments the methods further comprise removing the recombinant phage genome from the recombinant vector. In some embodiments the recombinant phage genome is removed from the recombinant vector by a method comprising, transforming the recombinant vector comprising the recombinant phage genome into competent phage host cells, and culturing the phage host cells under conditions sufficient for production of phage particles comprising the recombinant phage genome. In some embodiments the methods further comprise isolating the recombinant phage genome. In some embodiments the vector is a yeast artificial chromosome and the vector host cell is a yeast cell.

In a third aspect additional methods of making a recombinant phage genome are provided. In some embodiments the methods comprise providing a yeast artificial chromosome comprising a cloned phage genome, and inserting a heterologous nucleic acid sequence into the cloned phage genome to provide a recombinant phage genome. In some embodiments the heterologous nucleic acid sequence is inserted into the phage genome in vivo. In some embodiments the heterologous nucleic acid sequence is inserted into the phage genome in vitro. In some embodiments the methods further comprise removing the recombinant phage genome from the yeast artificial chromosome. In some embodiments the recombinant phage genome is removed from the yeast artificial chromosome by a method comprising transforming the yeast artificial chromosome into competent phage host cells, and selecting a recombinant phage genome that yields phage particles comprising the phage genome from transformed phage host cells.

In some embodiments of the second and third aspects, the heterologous nucleic acid sequence comprises 3.1 kilobases. In some embodiments the heterologous nucleic acid sequence comprises an open reading frame. In some embodiments the open reading frame encodes a marker that confers at least one phenotype selected from a selectable phenotype and a screenable phenotype on a vector host cell comprising the vector. In some embodiments the open reading frame encodes a marker that confers at least one phenotype selected from a selectable phenotype and a screenable phenotype on a phage host cell comprising the phage genome. In some embodiments the heterologous nucleic acid sequence comprises a second open reading frame. In some embodiments the open reading frame is operatively linked to an expression control sequence that directs expression of the open reading frame in at least one of a vector host cell and a phage host cell. In some embodiments the expression control sequence is endogenous to the phage genome. In some embodiments the expression control sequence is located within the heterologous nucleic acid sequence.

In some embodiments of the first, second, and third aspects, the methods comprise analyzing the sequence of the starting phage genome.

In some embodiments of the first, second, and third aspects, the methods do not comprise analyzing the sequence of the starting phage genome.

In a fourth aspect methods of making a phage are provided. In some embodiments a cloned and/or recombinant phage genome made by a method of this disclosure is transformed into a phage host cell and phage particles comprising the phage genome produced by the transformed phage host cells are isolated. In some embodiments the methods comprise providing a yeast artificial chromosome comprising a phage genome, transforming the yeast artificial chromosome into competent phage host cells, and isolating phage particles comprising the phage genome produced by the transformed phage host cells. In some embodiments the phage genome is recombinant.

In a fifth aspect a cloned phage genome made by a method of this disclosure is also provided.

In a sixth aspect a recombinant phage genome made by a method of this disclosure is also provided.

In a seventh aspect a phage comprising a genome made by a method of this disclosure is also provided.

In an eighth aspect a YAC comprising a cloned phage genome is also provided. In some embodiments the cloned phage genome is a recombinant phage genome comprising a heterologous nucleic acid sequence. In some embodiments the heterologous nucleic acid sequence is inserted into the cloned phage genome without deletion of endogenous phage genomic sequence. In some embodiments the heterologous nucleic acid sequence is inserted into the cloned phage genome and endogenous phage genomic sequence is deleted at the site of insertion. In some embodiments the heterologous nucleic acid sequence comprises 3.1 kilobases. In some embodiments the heterologous nucleic acid sequence comprises an open reading frame. In some embodiments the open reading frame encodes a marker that confers at least one phenotype selected from a selectable phenotype and a screenable phenotype on a vector host cell comprising the vector. In some embodiments the open reading frame encodes a marker that confers at least one phenotype selected from a selectable phenotype and a screenable phenotype on a phage host cell comprising the phage genome. In some embodiments the heterologous nucleic acid sequence comprises a second open reading frame. In some embodiments the open reading frame is operatively linked to an expression control sequence that directs expression of the open reading frame in at least one of a vector host cell and a phage host cell. In some embodiments the expression control sequence is endogenous to the phage genome. In some embodiments the expression control sequence is located within the heterologous nucleic acid sequence.

In a ninth aspect a vector host cell comprising a recombinant vector according to this disclosure is provided. In some embodiments the vector host cell is a yeast cell and the recombinant vector is a YAC.

BRIEF DESCRIPTION OF THE DRAWINGS

FIG. 3A shows the cassette structure and oligonucleotides that may be used to amplify the Luc gene, the Ura3 gene, and the truncated Luc* gene. FIG. 3B shows recombination events that those fragments will undergo with the cloned T3 phage genome when introduced into a yeast cell comprising a YAC that comprises the cloned genome. FIG. 3C shows the resulting phage genome structure following recombination. Note that the recombined genome initially comprises the Luc gene, the Ura3 gene, and the truncated Luc* gene. As shown in FIG. 3D, if selection for Ura3 (which acts as a selectable marker in yeast grown in the absence of uracil) is removed then recombination between the homologous sequences in the Luc gene and the truncated Luc* gene (represented by arrows in the figure) will occur and can be selected for using counter selection with 5-FOA (FIG. 3E).

DETAILED DESCRIPTION

Figure 1:
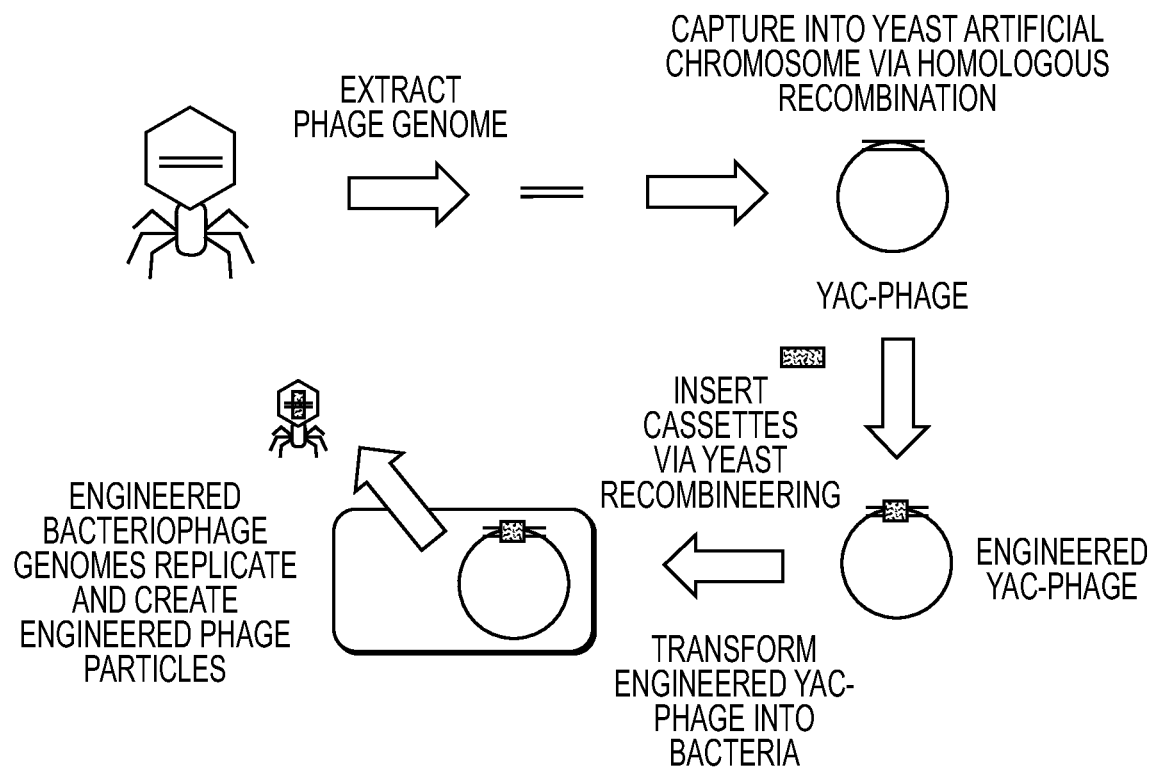
FIG. 1 shows an overview of a phage engineering platform that comprises the steps of extracting a starting phage genome, capturing the phage genome into a yeast artificial chromosome (YAC) to yield a YAC-phage, insertion of a heterologous cassette into the captured phage genome, and transformation of the engineered YAC-phage into a phage host cell capable of yielding phage particles comprising the engineered phage genome.

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art. Certain references and other documents cited herein are expressly incorporated herein by reference. Additionally, all UniProt/SwissProt records cited herein are hereby incorporated herein by reference. In case of conflict, the present specification, including definitions, will control. The materials, methods, and examples are illustrative only and not intended to be limiting.

The methods and techniques of the present disclosure are generally performed according to conventional methods well known in the art and as described in various general and more specific references that are cited and discussed throughout the present specification unless otherwise indicated. See, e.g., Clokie et al., *Bacteriophages: Methods and Protocols*, Vols. 1 and 2 (*Methods in Molecular Biology*, Vols. 501 and 502), Humana Press, New York, N.Y. (2009); Sambrook et al., *Molecular Cloning: A Laboratory Manual*, 3d ed., Cold Spring Harbor Laboratory Press, Cold Spring Harbor, N.Y. (2001); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol I, CRC Press (1976); Handbook of Biochemistry: Section A Proteins, Vol II, CRC Press (1976); *Essentials of Glycobiology*, Cold Spring Harbor Laboratory Press (1999).

This disclosure refers to sequence database entries (e.g., UniProt/SwissProt or GENBANK records) for certain protein and gene sequences that are published on the internet, as well as other information on the internet. The skilled artisan understands that information on the internet, including sequence database entries, is updated from time to time and that, for example, the reference number used to refer to a particular sequence can change. Where reference is made to a public database of sequence information or other information on the internet, it is understood that such changes can occur and particular embodiments of information on the internet can come and go. Because the skilled artisan can find equivalent information by searching on the internet, a reference to an internet web page address or a sequence database entry evidences the availability and public dissemination of the information in question.

Before the present vectors, genomes, cells, phage, compositions, methods, and other embodiments are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

The term "comprising" as used herein is synonymous with "including" or "containing," and is inclusive or open-ended and does not exclude additional, unrecited members, elements or method steps.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe).

As used herein, the term "isolated" refers to a substance or entity that has been (1) separated from at least some of the components with which it was associated when initially produced (whether in nature or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

The term "peptide" as used herein refers to a short polypeptide, e.g., one that typically contains less than about 50 amino acids and more typically less than about 30 amino acids. The term as used herein encompasses analogs and mimetics that mimic structural and thus biological function.

The term "polypeptide" encompasses both naturally-occurring and non-naturally occurring proteins, and fragments, mutants, derivatives and analogs thereof. A polypeptide may be monomeric or polymeric. Further, a polypeptide may comprise a number of different domains each of which has one or more distinct activities. For the avoidance of doubt, a "polypeptide" may be any length greater two amino acids.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from a cell in which it was synthesized.

The term "polypeptide fragment" as used herein refers to a polypeptide that has a deletion, e.g., an amino-terminal and/or carboxy-terminal deletion compared to a full-length polypeptide, such as a naturally occurring protein. In an embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, or at least 12, 14, 16 or 18 amino acids long, or at least 20 amino acids long, or at least 25, 30, 35, 40 or 45, amino acids, or at least 50 or 60 amino acids long, or at least 70 amino acids long.

The term "fusion protein" refers to a polypeptide comprising a polypeptide or fragment coupled to heterologous amino acid sequences. Fusion proteins are useful because they can be constructed to contain two or more desired functional elements that can be from two or more different proteins. A fusion protein comprises at least 10 contiguous amino acids from a polypeptide of interest, or at least 20 or 30 amino acids, or at least 40, 50 or 60 amino acids, or at least 75, 100 or 125 amino acids. The heterologous polypeptide included within the fusion protein is usually at least 6 amino acids in length, or at least 8 amino acids in length, or at least 15, 20, or 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, a protein has "homology" or is "homologous" to a second protein if the nucleic acid sequence that encodes the protein has a similar sequence to the nucleic acid sequence that encodes the second protein. Alternatively, a protein has homology to a second protein if the two proteins have similar amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, Methods Mol. Biol. 24:307-31 and 25:365-89.

The following six groups each contain amino acids that are conservative substitutions for one another: 1) Serine, Threonine; 2) Aspartic Acid, Glutamic Acid; 3) Asparagine, Glutamine; 4) Arginine, Lysine; 5) Isoleucine, Leucine, Methionine, Alanine, Valine, and 6) Phenylalanine, Tyrosine, Tryptophan.

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

An exemplary algorithm when comparing a particular polypeptide sequence to a database containing a large number of sequences from different organisms is the computer program BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

Exemplary parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62. The length of polypeptide sequences compared for homology will generally be at least about 16 amino acid residues, or at least about 20 residues, or at least about 24 residues, or at least about 28 residues, or more than about 35 residues. When searching a database containing sequences from a large number of different organisms, it may be useful to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, Methods Enzymol. 183:63-98 (1990). For example, percent sequence identity between amino acid sequences can be determined using FASTA with its default parameters (a word size of 2 and the PAM250 scoring matrix), as provided in GCG Version 6.1, herein incorporated by reference.

In some embodiments, polymeric molecules (e.g., a polypeptide sequence or nucleic acid sequence) are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% similar. The term "homologous" necessarily refers to a comparison between at least two sequences (nucleotides sequences or amino acid sequences). In some embodiments, two nucleotide sequences are considered to be homologous if the polypeptides they encode are at least about 50% identical, at least about 60% identical, at least about 70% identical, at least about 80% identical, or at least about 90% identical for at least one stretch of at least about 20 amino acids. In some embodiments, homologous nucleotide sequences are characterized by the ability to encode a stretch of at least 4-5 uniquely specified amino acids. Both the identity and the approximate spacing of these amino acids relative to one another must be considered for nucleotide sequences to be considered homologous. In some embodiments of nucleotide sequences less than 60 nucleotides in length, homology is determined by the ability to encode a stretch of at least 4-5 uniquely specified amino acids. In some embodiments, two protein sequences are considered to be homologous if the proteins are at least about 50% identical, at least about 60% identical, at least about 70% identical, at least about 80% identical, or at least about 90% identical for at least one stretch of at least about 20 amino acids.

As used herein, a "modified derivative" refers to polypeptides or fragments thereof that are substantially homologous in primary structural sequence to a reference polypeptide sequence but which include, e.g., in vivo or in vitro chemical and biochemical modifications or which incorporate amino acids that are not found in the reference polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}$I, $^{32}$P, $^{35}$S, and $^{3}$H, ligands that bind to labeled antiligands (e.g., antibodies), fluorophores, chemiluminescent agents, enzymes, and antiligands that can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., Current Protocols in Molecular Biology, Greene Publishing Associates (1992, and Supplements to 2002).

As used herein, "polypeptide mutant" or "mutein" refers to a polypeptide whose sequence contains an insertion, duplication, deletion, rearrangement or substitution of one or more amino acids compared to the amino acid sequence of a reference protein or polypeptide, such as a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the reference protein, and/or truncations of the amino acid sequence at either or both the amino or carboxy termini. A mutein may have the same or a different biological activity compared to the reference protein.

In some embodiments, a mutein has, for example, at least 85% overall sequence homology to its counterpart reference protein. In some embodiments, a mutein has at least 90% overall sequence homology to the wild-type protein. In other embodiments, a mutein exhibits at least 95% sequence identity, or 98%, or 99%, or 99.5% or 99.9% overall sequence identity.

As used herein, a "polypeptide tag for affinity purification" is any polypeptide that has a binding partner that can be used to isolate or purify a second protein or polypeptide sequence of interest fused to the first "tag" polypeptide. Several examples are well known in the art and include a His-6 tag [SEQ ID NO: 46], a FLAG epitope, a c-myc epitope, a Strep-TAGII, a biotin tag, a glutathione 5-transferase (GST), a chitin binding protein (CBP), a maltose binding protein (MBP), or a metal affinity tag.

As used herein, "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids. Thus, for example, a protein synthesized by a microorganism is recombinant, for example, if it is synthesized from an mRNA synthesized from a recombinant gene present in the cell.

The term "polynucleotide", "nucleic acid molecule", "nucleic acid", or "nucleic acid sequence" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

A "synthetic" RNA, DNA or a mixed polymer is one created outside of a cell, for example one synthesized chemically.

The term "nucleic acid fragment" as used herein refers to a nucleic acid sequence that has a deletion, e.g., a 5'-terminal or 3'-terminal deletion compared to a full-length reference nucleotide sequence. In an embodiment, the nucleic acid fragment is a contiguous sequence in which the nucleotide sequence of the fragment is identical to the corresponding positions in the naturally-occurring sequence. In some embodiments fragments are at least 10, 15, 20, or 25 nucleotides long, or at least 20, 30, 40, 50, 60, 70, 80, 90, 100, 110, 120, 130, 140, or 150 nucleotides long. In some embodiments a fragment of a nucleic acid sequence is a fragment of an open reading frame sequence. In some embodiments such a fragment encodes a polypeptide fragment (as defined herein) of the protein encoded by the open reading frame nucleotide sequence.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32, and even more typically at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, or at least about 90%, or at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point (Tm) for the specific DNA hybrid under a particular set of conditions. "Stringent washing" is performed at temperatures about 5° C. lower than the Tm for the specific DNA hybrid under a particular set of conditions. The Tm is the temperature at which 50% of the target sequence hybridizes to a perfectly matched probe. See Sambrook et al., Molecular Cloning: A Laboratory Manual, 2d ed., Cold Spring Harbor Laboratory Press, Cold Spring Harbor, N.Y. (1989), page 9.51. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65°

C. will occur at different rates depending on a number of factors including the length and percent identity of the sequences which are hybridizing.

As used herein, an "expression control sequence" refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to encompass, at a minimum, any component whose presence is essential for expression, and can also encompass an additional component whose presence is advantageous, for example, leader sequences and fusion partner sequences.

As used herein, "operatively linked" or "operably linked" expression control sequences refers to a linkage in which the expression control sequence is contiguous with the gene of interest to control the gene of interest, as well as expression control sequences that act in trans or at a distance to control the gene of interest.

As used herein, a "vector" is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors").

A "recombinant vector" is a vector into which a phage genome has been inserted. In some embodiments a starting phage genome is inserted. In some embodiments a recombinant phage genome is inserted. In some embodiments a starting phage genome is inserted and then is modified, in the vector, to create a recombinant phage genome in the vector.

The term "recombinant host cell" (or simply "recombinant cell" or "host cell"), as used herein, is intended to refer to a cell into which a recombinant nucleic acid such as a recombinant vector has been introduced. In some instances the word "cell" is replaced by a name specifying a type of cell. For example, a "recombinant microorganism" is a recombinant host cell that is a microorganism host cell. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "recombinant host cell," "recombinant cell," and "host cell", as used herein. A recombinant host cell may be an isolated cell or cell line grown in culture or may be a cell which resides in a living tissue or organism.

As used herein, "bacteriophage" refers to a virus that infects bacteria. Similarly, "archeophage" refers to a virus that infects archaea. The term "phage" is used to refer to both types of viruses but in certain instances as indicated by the context may also be used as shorthand to refer to a bacteriophage or archeophage specifically. Bacteriophage and archeophage are obligate intracellular parasites that multiply inside bacteria/archaea by making use of some or all of the host biosynthetic machinery (i.e., viruses that infect bacteria). Though different bacteriophages and archeophages may contain different materials, they all contain nucleic acid and protein, and can under certain circumstances be encapsulated in a lipid membrane. Depending upon the phage, the nucleic acid can be either DNA or RNA but not both and it can exist in various forms.

As used herein, "heterologous nucleic acid sequence" is any sequence placed at a location in the genome where it does not normally occur. A heterologous nucleic acid sequence may comprise a sequence that does not naturally occur in bacteria/archaea and/or phage or it may comprise only sequences naturally found in bacteria/archaea and/or phage, but placed at a non-normally occurring location in the genome. In some embodiments the heterologous nucleic acid sequence is not a natural phage sequence; in some embodiments it is a natural phage sequence, albeit from a different phage; while in still other embodiments it is a sequence that occurs naturally in the genome of the starting phage but is then moved to another site where it does not naturally occur, rendering it a heterologous sequence at that new site.

A "starting phage" or "starting phage genome" is a phage isolated from a natural or human made environment that has not been modified by genetic engineering, or the genome of such a phage.

A "recombinant phage" or "recombinant phage genome" is a phage that comprises a genome that has been genetically modified by insertion of a heterologous nucleic acid sequence into the genome, or the genome of the phage. In some embodiments the genome of a starting phage is modified by recombinant DNA technology to introduce a heterologous nucleic acid sequence into the genome at a defined site. In some embodiments the heterologous sequence is introduced with no corresponding loss of endogenous phage genomic nucleotides. In other words, if bases N1 and N2 are adjacent in the starting phage genome the exogenous sequence is inserted between N1 and N2. Thus, in the resulting recombinant genome the heterologous sequence is flanked by nucleotides N1 and N2. In some cases the heterologous sequence is inserted and endogenous nucleotides are removed or replaced with the exogenous sequence. For example, in some embodiments the exogenous sequence is inserted in place of some or all of the endogenous sequence which is removed. In some embodiments endogenous sequences are removed from a position in the phage genome distant from the site(s) of insertion of exogenous sequences.

A "phage host cell" is a cell that can be infected by a phage to yield progeny phage particles.

"Operatively linked" or "operably linked" expression control sequences refers to a linkage in which the expression control sequence is contiguous with coding sequences of interest to control expression of the coding sequences of interest, as well as expression control sequences that act in trans or at a distance to control expression of the coding sequence.

A "coding sequence" or "open reading frame" is a sequence of nucleotides that encodes a polypeptide or protein. The termini of the coding sequence are a start codon and a stop codon.

The term "expression control sequence" as used herein refers to polynucleotide sequences which affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

As used herein, a "selectable marker" is a marker that confers upon cells that possess the marker the ability to grow in the presence or absence of an agent that inhibits or stimulates, respectively, growth of similar cells that do not express the marker. Such cells can also be said to have a "selectable phenotype" by virtue of their expression of the selectable marker. For example, the ampicillin resistance gene (AmpR) confers the ability to grow in the presence of ampicillin on cells which possess and express the gene. (See Sutcliffe, J. G., *Proc Natl Acad Sci USA*. 1978 August; 75(8): 3737-3741.) Other nonlimiting examples include genes that confer resistance to chloramphenicol, kanamycin, and tetracycline. Other markers include URA3, TRP and LEU that allow growth in the absence of said uracil, tryptophan and leucine, respectively.

As used herein, a "screenable marker" is a detectable label that that can be used as a basis to identify cells that express the marker. Such cells can also be said to have a "screenable phenotype" by virtue of their expression of the screenable marker. Suitable markers include a radiolabel, a fluorescent label, a nuclear magnetic resonance active label, a luminescent label, a chromophore label, a positron emitting isotope for PET scanner, chemiluminescence label, or an enzymatic label. Fluorescent labels include but are not limited to, green fluorescent protein (GFP), fluorescein, and rhodamine. Chemiluminescence labels include but are not limited to, luciferase and β-galactosidase. Enzymatic labels include but are not limited to peroxidase and phosphatase. A histag may also be a detectable label. In some embodiments a heterologous nucleic acid is introduced into a cell and the cell then expresses a protein that is or comprises the label. For example, the introduced nucleic acid can comprise a coding sequence for GFP operatively linked to a regulatory sequence active in the cell.

As used herein, a "phage genome" includes naturally occurring phage genomes and derivatives thereof. Generally, the derivatives possess the ability to propagate in the same hosts as the parent. In some embodiments the only difference between a naturally occurring phage genome and a derivative phage genome is at least one of a deletion and an addition of nucleotides from at least one end of the phage genome if the genome is linear or at least one point in the genome if the genome is circular.

As used herein, a "vector host cell" is a cell that can host a given vector type through at least several cell division cycles. Thus, a vector host cell can replicate a vector introduced into the cell and partition copies of the vector to each daughter cell through at least several cell division cycles. For example, a yeast cell is a vector host cell for a yeast artificial chromosome (YAC) vector.

As used herein, a "phage host cell" is a cell that can form phage from a particular type of phage genomic DNA. In some embodiments the phage genomic DNA is introduced into the cell by infection of the cell by a phage. In some embodiments the phage genomic DNA is introduced into the cell using transformation or any other suitable technique. In some embodiments the phage genomic DNA is substantially pure when introduced into the cell. In some embodiments the phage genomic DNA is present in a vector when introduced into the cell. In one non-limiting exemplary embodiment the phage genomic DNA is present in the YAC that is introduced into the phage host cell. The phage genomic DNA is then copied and packaged into a phage particle following lysis of the phage host cell. The definition of "phage host cell" necessarily can vary from one phage to another. For example, *E. coli* may be a phage host cell for a particular type of phage while *Salmonella enterica* is not.

As used herein, a "competent phage host cell" is a phage host cell that a phage particle can infect, and in which the phage's genome can direct production of phage particles from the cell. Thus, not all "phage host cells" are "competent phage host cells," but all "competent phage host cells" are "phage host cells."

As used herein, the term "non-sequence specific process" used in relation to a process of insertion of a first nucleic acid sequence into a second nucleic acid sequence is a process in which the site of insertion in the second nucleic acid sequence is not determined prior to the insertion.

As used herein, a "transposase system" comprises a transposase enzyme or a nucleic acid capable of directing expression of the transposase, and a genetic element that can be mobilized by the enzyme. Typically the genetic element comprises sequences at either end necessary for mobilization and an internal heterologous sequence for insertion into a target nucleic acid. Non-limiting examples of transposase systems include Mos1 (mariner) (See Jacobsen et al., PNAS USA, Vol. 83, pp. 8684-8688 (1986)), Mu, Tn5 (kits and reagents available from Epicentre® (www.epicenre.com), and piggybac (See U.S. Pat. No. 6,218,185).

As used herein, a "pre-determined position" in reference to the site of insertion of a heterologous nucleic acid sequence into a second nucleic acid sequence, such as a phage genome, means a site that was selected prior to insertion of the heterologous nucleic acid sequence into the second nucleic acid sequence.

A. Phage

Bacteriophage and archeophage are obligate intracellular parasites that multiply inside bacteria/archaea by making use of some or all of the host biosynthetic machinery (i.e., viruses that infect bacteria/archaea). Though different phages may contain different materials, they all contain nucleic acid and protein, and may be covered by a lipid membrane. Depending upon the phage, the nucleic acid can be either DNA or RNA but not both and it can exist in various forms. The size of the nucleic acid varies depending upon the phage. The simplest phages only have genomes a few thousand nucleotides in size, while the more complex phages may have more than 100,000 nucleotides in their genome, in rare instances more than 1,000,000. The number of different kinds of protein and the amount of each kind of protein in the phage particle will vary depending upon the phage. The proteins function in infection and to protect the nucleic acid from nucleases in the environment.

Phages come in many different sizes and shapes. Most phages range in size from 24-200 nm in diameter. The head or capsid is composed of many copies of one or more different proteins. The nucleic acid is located in the head if it is present, which acts as a protective covering for it. Many but not all phages have tails attached to the phage head. The tail is a hollow tube through which the nucleic acid passes during infection. The size of the tail can vary and some phages do not even have a tail structure. In the more complex phages the tail is surrounded by a contractile sheath which contracts during infection of the bacterium. At the end of the tail, phages have a base plate and one or more tail fibers attached to it. The base plate and tail fibers are involved in the binding of the phage to the cell. Not all phages have base plates and tail fibers. In these instances other structures are involved in binding of the phage particle to the bacterium/archaea.

The first step in the infection process is the adsorption of the phage to the cell. This step is mediated by the tail fibers or by some analogous structure on those phages that lack tail fibers and it is reversible. The tail fibers attach to specific receptors on the cell and the host specificity of the phage (i.e. the bacteria/archaea that it is able to infect) is usually determined by the type of tail fibers that a phage has. The nature of the bacterial/archaeal receptor varies for different bacteria/archaea. Examples include proteins on the outer surface of the cell, LPS, pili, and lipoprotein. These receptors are on the cell for other purposes and phage have evolved to use these receptors for infection.

The attachment of the phage to the cell via the tail fibers is a weak one and is reversible. Irreversible binding of phage to a cell is mediated by one or more of the components of the base plate. Phages lacking base plates have other ways of becoming tightly bound to the cell.

The irreversible binding of the phage to the cell results in the contraction of the sheath (for those phages which have a sheath) and the hollow tail fiber is pushed through the bacterial/archaeal envelope. Phages that don't have contractile sheaths use other mechanisms to get the phage particle through the bacterial/archaeal envelope. Some phages have enzymes that digest various components of the envelope.

When the phage has gotten through the envelope the nucleic acid from the head passes through the hollow tail and enters the cell. Usually, the only phage component that actually enters the cell is the nucleic acid. The remainder of the phage remains on the outside of the cell. There are some exceptions to this rule. This is different from animal cell viruses in which most of the virus particle usually gets into the cell.

Lytic or virulent phages are phages which can only multiply on bacteria/archaea and kill the cell by lysis at the end of the life cycle. The lifecycle of a lytic phage begins with an eclipse period. During the eclipse phase, no infectious phage particles can be found either inside or outside the cell. The phage nucleic acid takes over the host biosynthetic machinery and phage specified mRNAs and proteins are made. There is an orderly expression of phage directed macromolecular synthesis, just as one sees in animal virus infections. Early mRNAs code for early proteins which are needed for phage DNA synthesis and for shutting off host DNA, RNA and protein biosynthesis. In some cases the early proteins actually degrade the host chromosome. After phage DNA is made late mRNAs and late proteins are made. The late proteins are the structural proteins that comprise the phage as well as the proteins needed for lysis of the bacterial cell. Next, in the intracellular accumulation phase the nucleic acid and structural proteins that have been made are assembled and infectious phage particles accumulate within the cell. During the lysis and release phase the bacteria/archaea begin to lyse due to the accumulation of the phage lysis protein and intracellular phage are released into the medium. The number of particles released per infected cell can be as high as 1000 or more.

Lytic phage may be enumerated by a plaque assay. A plaque is a clear area which results in a lawn of bacterial/archaea grown on a solid media from the lysis of bacteria/archaea. The assay is performed at a low enough concentration of phage that each plaque arises from a single infectious phage. The infectious particle that gives rise to a plaque is called a PFU (plaque forming unit).

Lysogenic or temperate phages are those that can either multiply via the lytic cycle or enter a quiescent state in the cell. In this quiescent state most of the phage genes are not transcribed; the phage genome exists in a repressed state. The phage DNA in this repressed state is called a prophage because it is not a phage but it has the potential to produce phage. In most cases the phage DNA actually integrates into the host chromosome and is replicated along with the host chromosome and passed on to the daughter cells. The cell harboring a prophage is not adversely affected by the presence of the prophage and the lysogenic state may persist indefinitely. The cell harboring a prophage is termed a lysogen.

The mechanisms of lysongeny differ between phage. In a classic example, phage lambda, lambda DNA is a double stranded linear molecule with small single stranded regions at the 5' ends. These single stranded ends are complementary (cohesive ends) so that they can base pair and produce a circular molecule. In the cell the free ends of the circle can be ligated to form a covalently closed circle. A site-specific recombination event, catalyzed by a phage coded enzyme, occurs between a particular site on the circularized phage DNA and a particular site on the host chromosome. The result is the integration of the phage DNA into the host chromosome. A phage coded protein, called a repressor, is made which binds to a particular site on the phage DNA, called the operator, and shuts off transcription of most phage genes except the repressor gene. The result is a stable repressed phage genome which is integrated into the host chromosome. Each temperate phage will only repress its own DNA and not that from other phage, so that repression is very specific (immunity to superinfection with the same phage).

Anytime a lysogenic bacterium/archaea is exposed to adverse conditions, the lysogenic state can be terminated. This process is called induction. Conditions which favor the termination of the lysogenic state include: desiccation, exposure to UV or ionizing radiation, exposure to mutagenic chemicals, etc. Adverse conditions lead to the production of proteases (rec A protein) which destroy the repressor protein. This in turn leads to the expression of the phage genes, reversal of the integration process and lytic multiplication.

In some embodiments of this disclosure a starting phage genome comprises at least 5 kilobases (kb), at least 10 kb, at least 15 kb, at least 20 kb, at least 25 kb, at least 30 kb, at least 35 kb, at least 40 kb, at least 45 kb, at least 50 kb, at least 55 kb, at least 60 kb, at least 65 kb, at least 70 kb, at least 75 kb, at least 80 kb, at least 85 kb, at least 90 kb, at least 95 kb, at least 100 kb, at least 105 kb, at least 110 kb, at least 115 kb, at least 120 kb, at least 125 kb, at least 130 kb, at least 135 kb, at least 140 kb, at least 145 kb, at least 150 kb, at least 175 kb, at least 200 kb, at least 225 kb, at least 250 kb, at least 275 kb, at least 300 kb, at least 325 kb, at least 350 kb, at least 325 kb, at least 350 kb, at least 375 kb, at least 400 kb, at least 425 kb, at least 450 kb, at least 475 kb, at least 500 kb, or more.

In some embodiments of this disclosure a starting phage is a member of an order selected from Caudovirales, Microviridae, Corticoviridae, Tectiviridae, Leviviridae, Cystoviridae, Inoviridae, Lipothrixviridae, Rudiviridae, Plasmaviridae, and Fuselloviridae. In some embodiments the phage is a member of the order Caudovirales and is a member of a family selected from Myoviridae, Siphoviridae, and Podoviridae.

In some embodiments of this disclosure the phage is able to productively infect archaea. In some embodiments the archaea is a Euryarcheota. In some embodiments the archaea is a Crenarcheota. In some embodiments of this disclosure the phage is able to productively infect bacteria. In some embodiments the bacteria is a member of a phyla selected from Actinobacteria, Aquificae, Armatimonadetes, Bacteroidetes, Caldiserica, Chlamydiae, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Nitrospirae, Planctomycetes, Proteobacteria, Spirochaetes, Synergistets, Tenericutes, Thermodesulfobacteria, Thermotogae. In some embodiments the phage is able to productively infect at least one Firmicutes selected from *Bacillus, Listeria, Staphylococcus*. In some embodiments the phage is able to productively infect at least one Proteobacteria selected from *Acidobacillus, Aeromonas, Burkholderia, Neisseria, Shewanella, Citrobacter, Enterobacter, Erwinia, Escherichia, Klebsiella, Kluyvera, Morganella, Salmonella, Shigella, Yersinia, Coxiella, Rickettsia, Legionella, Avibacterium, Haemophilus, Pasteurella, Acinetobacter, Moraxella, Pseudomonas, Vibrio, Xanthomonas*. In some embodiments the phage is able to productively infect at least one Tenericutes selected from *Mycoplasma, Spiroplasma*, and *Ureaplasma*.

Phage genomes comprise end structures that present challenges to cloning an intact phage genome that retains the ability to infect target microbes and produce daughter phage. The methods of this disclosure are particularly useful because they enable the cloning of phage genomes with intact ends such that the cloned phage retain the ability to infect target microbes and produce daughter phage. In some embodiments the phage genome comprises terminal perfect repeats. In some embodiments the phage genome comprises imperfect repeats.

In some embodiments the repeats have a unit size of from 3 nucleotides to 20 kb. That is, each copy of the repeat "unit" is that long. In some embodiments the repeats have a unit size of from 5 nucleotides to 1 kb. In some embodiments the repeats have a unit size of from 10 nucleotides to 1 kb. In some embodiments the repeats have a unit size of from 25 nucleotides to 1 kb. In some embodiments the repeats have a unit size of from 50 nucleotides to 1 kb. In some embodiments the repeats have a unit size of from 100 nucleotides to 1 kb. In some embodiments the repeats have a unit size of from 250 nucleotides to 1 kb. In some embodiments the repeats have a unit size of from 500 nucleotides to 1 kb. In some embodiments the repeats have a unit size of from 100 nucleotides to 5 kb. In some embodiments the repeats have a unit size of from 250 nucleotides to 5 kb. In some embodiments the repeats have a unit size of from 500 nucleotides to 5 kb. In some embodiments the repeats have a unit size of from 1 kb to 5 kb. In some embodiments the repeats have a unit size of from 2 kb to 5 kb. In some embodiments the repeats have a unit size of from 3 kb to 5 kb. In some embodiments the repeats have a unit size of from 4 kb to 5 kb. In some embodiments the repeats have a unit size of from 100 nucleotides to 10 kb. In some embodiments the repeats have a unit size of from 250 nucleotides to 10 kb. In some embodiments the repeats have a unit size of from 500 nucleotides to 10 kb. In some embodiments the repeats have a unit size of from 1 kb to 10 kb. In some embodiments the repeats have a unit size of from 2 kb to 10 kb. In some embodiments the repeats have a unit size of from 5 kb to 10 kb.

In some embodiments the repeats have a total length (at least terminus) of from 3 nucleotides to 20 kb. In some embodiments the repeats have a total length of from 10 nucleotides to 20 kb. In some embodiments the repeats have a total length of from 25 nucleotides to 20 kb. In some embodiments the repeats have a total length of from 50 nucleotides to 20 kb. In some embodiments the repeats have a total length of from 100 nucleotides to 20 kb. In some embodiments the repeats have a total length of from 250 nucleotides to 20 kb. In some embodiments the repeats have a total length of from 500 nucleotides to 20 kb. In some embodiments the repeats have a total length of from 1 kb to 20 kb. In some embodiments the repeats have a total length of from 2 kb to 20 kb. In some embodiments the repeats have a total length of from 3 kb to 20 kb. In some embodiments the repeats have a total length of from 4 kb to 20 kb. In some embodiments the repeats have a total length of from 5 kb to 20 kb. In some embodiments the repeats have a total length of from 10 kb to 20 kb. In some embodiments the repeats have a total length of from 1 kb to 2 kb. In some embodiments the repeats have a total length of from 1 kb to 3 kb. In some embodiments the repeats have a total length of from 1 kb to 4 kb. In some embodiments the repeats have a total length of from 1 kb to 5 kb. In some embodiments the repeats have a total length of from 2 kb to 4 kb. In some embodiments the repeats have a total length of from 3 kb to 5 kb. In some embodiments the repeats have a total length of from 4 kb to 6 kb. In some embodiments the repeats have a total length of from 5 kb to 10 kb.

B. Phage Capture

1. Isolation of Phage Genomes

Any suitable method may be used to isolate phage genomes from phage cultures and/or isolated phage and/or concentrated phage preparations. For example one or more of the following column-based, PEG-based, filter-based, and cesium chloride centrifugation methods may be used.

Column-Based:

High-titer lysates of a phage culture are further concentrated via chromatography based on charge and/or affinity, allowing the concentration of large volumes of lysate into very small volumes. Passing the phages over a column, and then eluting into a small volume provides the material for DNA-harvesting of phages for further genome manipulation.

PEG-Based:

The presence of high-concentrations of polyethylene glycol allows precipitation of active phage particles from a lower-titer, high volume of phage material. This type of standard treatment allows greater than one hundred-fold concentration of phage lysates, allowing large amounts of DNA to be recovered for further genome manipulation.

Filter-Based:

Filtering lysates to remove large cell debris, followed by filtration in the 100 kDa size range allows the retention of phage particles, while losing water and salts in the phage lysate preparation. This is yet another technique for concentrating phages for isolation of large amounts of DNA for further phage genome manipulation.

Cesium Chloride Centrifugation:

Concentrated lysates are further purified by treating them with DNases to remove contaminating host DNA, followed by centrifugation in a cesium chloride gradient to purify the phage particles away from the cell debris. These highly purified lysates will produce very clean DNA for later manipulation.

Purification of DNA:

Regardless of the purification method of phage particles, phage lysates are optionally treated with proteases and chloroform to remove the phage coats, followed by either column-based DNA purification or ethanol precipitation of the recovered DNA. All DNA recovered at this step is ready for further capture and manipulation as outlined below.

Optional Sequencing of Phage Genomic DNA:

If the starting phage genomic sequence is unknown, the following process may optionally be used to generate a complete sequence:

First, next generation sequencing techniques may be used to generate contigs. Such methods generate large amounts of data that can be used to assemble contiguous pieces of phage sequence. This sequence is often not sufficient to close an entire phage genome with a single pass.

Remaining gaps may be filled using PCR-based techniques. Primers designed to anneal to the ends of contigs can be used in combination to do PCR on the phage genomic DNA. Only primers from contigs that are adjacent to each other will amplify a product. These PCR products can be sequenced by traditional Sanger sequencing to close the gaps between contigs.

Modified Sanger sequencing can be done directly off of phage genomic DNA. This technique can be used to sequence off of the ends of the phage given that PCR cannot be used to capture this final sequence. This will complete the phage genomic sequence.

2. Capture of Phage Genomes in Yeast Artificial Chromosomes

Isolated phage genomes are then captured in a vector. Examples of suitable vectors include bacterial artificial chromosomes (BACs) and yeast artificial chromosomes (YACs).

a. Homologous Recombination of Purely Linear Phage Genomes or Linear Phage Genomes with Imperfect Repeats Using Short Oligonucleotide Duplexes Bacteriophage for which the genome sequence is known provide a means to recombine the genome into a circular yeast artificial chromosome (YAC) using double strand break repair or other modes of recombination in yeast such as *S. cerevisae*. This method may be used for phages with purely linear genomes or linear phage genomes with imperfect repeats at the ends. A replicating yeast vector with a selectable marker is first linearized and "stitching" oligonucleotides are designed that contain sequence from the 3' ends of the linear bacteriophage genome as well as DNA flanking the double strand break in the yeast vector. Suitable oligonucleotides are for example from 20 to 2 kb long, such as 20 to 500 bp long, 50 to 500 bp long, 100 to 500 bp long, 200 to 500 bp long, 100 to 750 bp long, 250 bp to 1 kb long, and 500 bp to 2 kb long. The phage genomic DNA, stitching oligonucleotides, and a linearized yeast vector are cotransformed into competent yeast cells and plated on selective media. This procedure represents a clone DNA or die strategy that provides a way of selecting for those linearized vectors that have formed circles through DNA recombination via homologous sequences at the ends of vector and the phage genome. Colonies of yeast able to grow on selective media are then screened for presence of the junctions between the YAC DNA and the phage DNA, a DNA structure that only occurs if cloning of the phage DNA has been successful.

b. Homologous Recombination of Linear Phage Genomes with Perfect Repeats.

To capture phages with linear phage genomes that have perfect repeats at their ends, oligonucleotide duplexes may be used. The duplexes generally contain a portion that is homologous to the vector and a portion that is homologous to the phage genome, to stimulate homologous recombination between the vector and the phage genome for capture. The oligonucleotides are typically from 40 bases to 5 kb long, such as from 40 to 80 bases, from 50 to 100 bases, from 60 to 120 bases, from 80 to 160 bases, from 100 to 200 bases, from 200 to 400 bases, from 300 to 600 bases, from 400 to 800 bases, from 500 bases to 1 kb, from 1 to 2 kb or from 2 to 5 kb long.

These oligonucleotide duplexes are typically designed to capture varying portions of the phage genome. For example, in linear phage genomes with relatively short perfect repeats (for example, R-GGG-R, where R represents the perfect repeats and GGG represents the non-repeated phage genome sequence), 100% of the unique genome sequence can be captured by capturing one repeat with the non-repeated genome (for example R-GGG) or more than 100% of the unique genome sequence by capturing both repeats with the non-repeated genome (for example, R-GGG-R).

C. End Structures of Captured Phage Genomes.

In some embodiments the full length phage genome is captured. In some embodiments from 1 nucleotide to 20 kb of sequence at one or both ends of the genome is absent from the captured genome. In some embodiments at least 2, 3, 4, 5 or 10 nucleotides of sequence at one or both ends of the genome is absent from the captured genome. In some embodiments at least 20, 40, 60, 80, 100, 200, 300, 400, 500, 600, 700, 800, 900, or 1,000 nucleotides of sequence at one or both ends of the genome is absent from the captured genome. In some embodiments from 1 to 10 nucleotides, from 5 to 20 nucleotides, from 10 to 25 nucleotides, from 20 to 50 nucleotides, from 50 to 100 nucleotides, from 100 to 250 nucleotides, from 250 to 500 nucleotides, or from 500 to 1,000 nucleotides of sequence at one or both ends of the genome is absent from the captured genome. In some embodiments an integer number of repeats present at an end of the phage genome is absent from the captured genome. That is, if the phage naturally comprises 10 complete repeats of a sequence at each end of its genome one or both ends of the captured genome may comprise fewer than 10 complete repeats. In all cases, any modifications of the phage genome at one end may be the same as a modification at the other end or may be different, and one end may be modified even if the other is not.

In some embodiments from 1 nucleotide to 20 kb of sequence at one or both ends of the genome is duplicated. In some embodiments at least 2, 3, 4, 5 or 10 nucleotides of sequence at one or both ends of the genome is duplicated in the captured genome. In some embodiments at least 20, 40, 60, 80, 100, 200, 300, 400, 500, 600, 700, 800, 900, or 1,000 nucleotides of sequence at one or both ends of the genome is duplicated in the captured genome. In some embodiments from 1 to 10 nucleotides, from 5 to 20 nucleotides, from 10 to 25 nucleotides, from 20 to 50 nucleotides, from 50 to 100 nucleotides, from 100 to 250 nucleotides, from 250 to 500 nucleotides, or from 500 to 1,000 nucleotides of sequence at one or both ends of the genome is duplicated in the captured genome. In some embodiments an integer number of repeats present at an end of the phage genome is duplicated in the captured genome. That is, if the phage naturally comprises 10 complete repeats of a sequence at each end of its genome one or both ends of the captured genome may comprise more than 10 complete repeats. In all cases, any modifications of the phage genome at one end may be the same as a modification at the other end or may be different, and one end may be modified even if the other is not.

3. Detection of Captured Phage Genomes a. PCR-Based Methods.

Primers may be used to enable PCR-based confirmation of captured phage genomes. For example, if one primer is specific for a portion of the YAC vector just outside the region of the captured phage and another primer is specific for a portion of the phage genome, these primers should together amplify a band to verify that the proper phage-YAC capture and junctions are present in a vector.

b. Direct Sequencing.

An alternative is to directly sequence the captured phage genomes to confirm the presence of the phage DNA inside the vector.

c. Restriction Digestion.

Captured phage genomes may also be identified and characterized using restriction digestion and gel electrophoresis.

d. Phi29/Sequencing Readout.

Typically, the YAC bearing the phage genome is not maintained in high copy number per cell. To facilitate assaying for the presence of phage and engineered phage the YAC may be amplified using a DNA polymerase from bacteriophage Phi29 that can copy the genome in vitro. These substrates may then be used for transformation and sequencing.

e. Phi29/RFLP Readout

Amplification of the phage-YACs with Phi29 polymerase allows for analysis with restriction enzymes to identify Restriction Fragment Length Polymorphisms (RFLPs) for rapid whole genome analysis. These products are run on agarose gels and analyzed via ethidium bromide staining.

C. Engineering Captured Phage Genomes

In some embodiments a heterologous nucleic acid sequence is inserted into a starting phage genome to create a recombinant phage genome. In some embodiments the recombinant phage genome is further modified to create a different recombinant phage genome.

1. Heterologous Nucleic Acid Sequences

The heterologous nucleic acid sequence may be any nucleic acid sequence. In some embodiments the length of the heterologous nucleic acid sequence is at least 100 bases, at least 200 based, at least 300 bases, at least 400 bases, at least 500 bases, at least 600 bases, at least 700 bases, at least 800 bases, at least 900 bases, at least 1 kilobase (kb), at least 1.1 kb, at least 1.2 kb, at least 1.3 kb, at least 1.4 kb, at least 1.5 kb, at least 1.6 kb, at least 1.7 kb, at least 1.8 kb, at least 1.9 kb, at least 2.0 kb, at least 2.1 kb, at least 2.2 kb, at least 2.3 kb, at least 2.4 kb, at least 2.5 kb, at least 2.6 kb, at least 2.7 kb, at least 2.8 kb, at least 2.9 kb, at least 3.0 kb, at least 3.1 kb, at least 3.2 kb, at least 3.3 kb, at least 3.4 kb, at least 3.5 kb, at least 3.6 kb, at least 3.7 kb, at least 3.8 kb, at least 3.9 kb, at least 4.0 kb, at least 4.5 kb, at least 5.0 kb, at least 5.5 kb, at least 5.5 kb, at least 6.0 kb, at least 6.5 kb, at least 7.0 kb, at least 7.5 kb, at least 8.0 kb, at least 8.5 kb, at least 9.0 kb, at least 9.5 kb, at least 10 kb, or more. In some such embodiments the heterologous nucleic acid sequence comprises a length that is less than or equal to the maximum length of heterologous nucleic acid sequence that can be packaged into a phage particle comprising the phage genome. In some such embodiments the heterologous nucleic acid sequence comprises a length that is less than or equal to a length chose from 1 kb, 2 kb, 3 kb, 4 kb, 5 kb, 6 kb, 7 kb, 8 kb, 9 kb, and 10 kb.

In some embodiments the length of the heterologous nucleic acid sequence is from 100 to 500 bases, from 200 to 1,000 bases, from 500 to 1,000 bases, from 500 to 1,500 bases, from 1 kb to 2 kb, from 1.5 kb to 2.5 kb, from 2.0 kb to 3.0 kb, from 2.5 kb to 3.5 kb, from 3.0 kb to 4.0 kb, from 3.5 kb to 4.5 kb, from 4.0 kb to 5.0 kb, from 4.5 kb to 5.5 kb, from 5.0 kb to 6.0 kb, from 5.5 kb to 6.5 kb, from 6.0 kb to 7.0 kb, from 6.5 kb to 7.5 kb, from 7.0 kb to 8.0 kb, from 7.5 kb to 8.5 kb, from 8.0 kb to 9.0 kb, from 8.5 kb to 9.5 kb, or from 9.0 kb to 10.0 kb.

In some embodiments the ratio of the length of the heterologous nucleic acid sequence to the total length of the genome of the recombinant phage is at least 0.05, at least 0.10, at least 0.15, at least 0.20, or at least 0.25. In some embodiments the ratio of the length of the genome of the recombinant phage to the length of the genome of the corresponding starting phage is at least 1.05, at least 1.10, at least 1.15, at least 1.20, or at least 1.25.

In some embodiments the heterologous nucleic acid sequence is inserted into the starting phage genome with no loss of endogenous starting phage genome sequence. In some embodiments the inserted heterologous nucleic acid sequence replaces endogenous starting phage genome sequence. In some such embodiments the heterologous nucleic acid sequence replaces an amount of endogenous genomic sequence that is less than the length of the heterologous nucleic acid sequence. Thus, the length of the recombinant phage genome is longer than the length of the starting phage genome. In some such embodiments the heterologous nucleic acid sequence replaces an amount of endogenous genomic sequence that is greater than the length of the heterologous nucleic acid sequence. Thus, the length of the recombinant phage genome is shorter than the length of the starting phage genome. In some such embodiments the heterologous nucleic acid sequence replaces an amount of endogenous genomic sequence that is equal to the length of the heterologous nucleic acid sequence.

In some embodiments the heterologous nucleic acid sequence comprises an first open reading frame.

In some embodiments the open reading frame encodes a marker that confers at least one phenotype on a vector host cell comprising the vector selected from a selectable phenotype and a screenable phenotype. In such embodiments the vector comprises an expression expression control sequence capable of directing expression of the open reading frame in the vector host cell. In some embodiments the selectable phenotype or the screenable phenotype is used to identify a host cell that comprises the vector comprising the phage genome comprising the open reading frame encoding the marker that confers at least one phenotype on a vector host cell comprising the vector selected from a selectable phenotype and a screenable phenotype. In some embodiments a portion of the vector outside of the phage genome comprises an open reading frame encoding a marker that confers at least one phenotype on a vector host cell comprising the vector selected from a selectable phenotype and a screenable phenotype. In some embodiments both the vector outside of the phage genome and the heterologous nucleic acid sequence inserted into the phage genome encode such a marker. In some embodiments the marker encoded by the open reading frame in the vector sequences and the marker encoded by the open reading frame in the heterologous nucleic acid sequence inserted into the phage genome are different.

In some embodiments the open reading frame encodes a protein that confers a phenotype of interest on a phage host cell expressing it. In some embodiments the phenotype of interest is simply expression of the expression product of the open reading frame. In some embodiments the phenotype of interest is a change in a structural feature of the phage host cell. In some embodiments the phenotype of interest is expression of a marker that confers at least one phenotype on a phage host cell comprising the phage genome selected from a selectable phenotype and a screenable phenotype. In such embodiments the open reading frame is operatively linked to an expression control sequence capable of directing expression of the open reading frame in a phage host cell. The expression control sequence may be located in the heterologous nucleic acid sequence or it may be in the endogenous phage genome sequence (i.e., it may be a sequence present in the starting phage genome). For example, the open reading frame may be inserted into the phage genome downstream of or in the place of an endogenous phage open reading frame sequence.

In some embodiments the open reading frame encodes a protein that serves as a marker that can be identified by screening of phage host cells infected by a recombinant phage comprising a heterologous nucleic acid sequence comprising the open reading frame. Examples of such markers include by way of example and without limitation: a radiolabel, a fluorescent label, a nuclear magnetic resonance active label, a luminescent label, a chromophore label, a positron emitting isotope for PET scanner, chemiluminescence label, or an enzymatic label. Fluorescent labels include but are not limited to, green fluorescent protein (GFP), fluorescein, and rhodamine. Chemiluminescence labels include but are not limited to, luciferase and β-galactosidase. Enzymatic labels include but are not limited to peroxidase and phosphatase. A Histag can also be used as a detectable label. In some embodiments a heterologous nucleic acid is introduced into a cell and the cell then expresses a protein that is or comprises the label. In some embodiments the open reading frame encodes a protein that is not normally produced by the phage host cell. Such a protein can be used as a marker that can be identified by screening, for example, by detecting the protein using an immunoassay. In some embodiments the screenable marker is detected in an assay to identify the presence of phage host cells in a sample. For example, the phage host cells can be a bacterial cell type that contaminates a food processing plant and detection of expression of the screenable marker in the cells following mixing of the recombinant phage with the sample can be used as an assay to detect contamination of the food processing plant by the phage host cells.

In some embodiments the open reading frame encodes a protein selected from a nuclease, endonuclease, protease, glycosidase, glycanase, hydrolase, lyase, esterase, phosphodiesterase, cellulase, lysin, and kinase. In some embodiments the protein is any protein other than at least one of a nuclease, endonuclease, protease, glycosidase, glycanase, hydrolase, lyase, esterase, phosphodiesterase, cellulase, lysin, and kinase.

In some embodiments the open reading frame encodes a protein listed in Table 1.

TABLE 1

| Common Name of Protein | EC | Substrate |
| --- | --- | --- |
| Nattokinase | 3.4.21.62 | protein, amyloids |
| Dispersin B | 3.2.1.52 | beta-1,6-N-acetyl-D-glucosamine |
| Alginate lyase | 4.2.2.3 | alginate |
| Alginate lyase | 4.2.2.11 | alginate |
| NucA | 3.1.30.2 | DNA, RNA |

TABLE 1-continued

| Common Name of Protein | EC | Substrate |
| --- | --- | --- |
| Endoglucanase | 3.2.1.4 | cellulose, lichenin, cereal beta-D-glucans |
| Subtilisin | 3.4.21.62 | protein |
| AlpP | | autolysis |
| Dnase A | | DNA, RNA |
| Aqualysin | 3.4.21.62 | protein |
| endX | 3.1.21.— | DNA |
| Subtilisin-like protease | | protein |
| glucan endo-1,3-beta-glucosidase A1 | 3.2.1.39 | beta-1,3-glucans in fungal cell walls |
| Thermonuclease | 3.1.31.1 | DNA, RNA |
| Mycolysin | 3.4.24.31 | protein, hydrophobic residues in P1' |
| DNAase I | 3.1.21.1 | DNA |
| Proteinase K | 3.4.21.64 | protein |
| Streptogrysin-C | 3.4.21.— | protein, similar to chymotrypsin, possibly specialized for chitin-like proteins |
| Streptogrysin-D | 3.4.21.— | protein large aliphatic or aromatic amino acids |
| Streptogrisin-A | 3.4.21.80 | protein, large aliphatic or aromatic amino acids |
| Streptogrisin-B | 3.4.21.81 | protein, large aliphatic or aromatic amino acids |
| xanthan lyase | | xanthan |
| beta-D-glucanase | | xanthan |
| ManA | | endo-beta-1,4-mannose |
| Quorum-sensing molecules | | |
| Gellan lyase | | gellan |
| Sphinganase | | gellan and similar polymers |

In some embodiments the open reading frame encodes a screenable marker that may be used to detect phage host cells that express it. Such cells can also be said to have a screenable phenotype by virtue of their expression of the screenable marker. Any molecule that can be differentially detected upon expression in a phage host cell may serve as a screenable marker in this context. A screenable marker may be a nucleic acid molecule or a portion thereof, such as an RNA or a DNA molecule that is single or double stranded. Alternatively, a screenable marker may be a protein or a portion thereof. Suitable protein markers include enzymes that catalyzes formation of a detectable reaction product. An example is a chemiluminescent protein such as luciferase or variations, such as luxAB, and β-galactosidase. Another example is the horseradish peroxidase enzyme. Proteins used to generate a luminescent signal fall into two broad categories: those that generate light directly (luciferases and related proteins) and those that are used to generate light indirectly as part of a chemical cascade (horseradish peroxidase). The most common bioluminescent proteins used in biological research are aequorin and luciferase. The former protein is derived from the jellyfish *Aequorea victoria* and can be used to determine calcium concentrations in solution. The luciferase family of proteins has been adapted for a broad range of experimental purposes. Luciferases from firefly and *Renilla* are the most commonly used in biological research. These proteins have also been genetically separated into two distinct functional domains that will generate light only when the proteins are closely co-localized. A variety of emission spectrum-shifted mutant derivatives of both of these proteins have been generated over the past decade. These have been used for multi-color imaging and co-localization within a living cell. The other groups of proteins used to generate chemiluminescent signal are peroxidases and phosphatases. Peroxidases generate peroxide that oxidizes luminol in a reaction that generates light. The most widely used of these is horseradish peroxidase (HRP), which has been used extensively for detection in western blots and ELISAs. A second group of proteins that have been employed in a similar fashion are alkaline phosphatases, which remove a phosphate from a substrate molecule, destabilizing it and initiating a cascade that results in the emission of light.

Other suitable screenable markers include fluorescent proteins. Fluorescent proteins include but are not limited to blue/UV fluorescent proteins (for example, TagBFP, Azurite, EBFP2, mKalama1, Sirius, Sapphire, and T-Sapphire), cyan fluorescent proteins (for example, ECFP, Cerulean, SCFP3A, mTurquoise, monomeric Midoriishi-Cyan, TagCFP, and mTFP1), green fluorescent proteins (for example, EGFP, Emerald, Superfolder GFP, Monomeric Azami Green, TagGFP2, mUKG, and mWasabi), yellow fluorescent proteins (for example, EYFP, Citrine, Venus, SYFP2, and TagYFP), orange fluorescent proteins (for example, Monomeric Kusabira-Orange, mKOκ, mKO2, mOrange, and mOrange2), red fluorescent proteins (for example, mRaspberry, mCherry, mStrawberry, mTangerine, tdTomato, TagRFP, TagRFP-T, mApple, and mRuby), far-red fluorescent proteins (for example, mPlum, HcRed-Tandem, mKate2, mNeptune, and NirFP), near-IR fluorescent proteins (for example, TagRFP657, IFP1.4, and iRFP), long stokes-shift proteins (for example, mKeima Red, LSS-mKate1, and LSS-mKate2), photoactivatable fluorescent proteins (for example, PA-GFP, PAmCherry1, and PATagRFP), photoconvertible fluorescent proteins (for example, Kaede (green), Kaede (red), KikGR1 (green), KikGR1 (red), PS-CFP2, PS-CFP2, mEos2 (green), mEos2 (red), PSmOrange, and PSmOrange), and photoswitchable fluorescent proteins (for example, Dronpa). Several variants and alternatives to the listed examples are also well known to those of skill in the art and may be substituted in appropriate applications.

Other suitable markers include epitopes. For example, a protein comprising an epitope that can be detected with an antibody or other binding molecule is an example of a screenable marker. An antibody that recognizes the epitope may be directly linked to a signal generating moiety (such as by covalent attachment of a chemiluminescent or fluorescent protein) or it can be detected using at least one additional binding reagent such as a secondary antibody, directly linked to a signal generating moiety, for example. In some embodiments the epitope is not present in the proteins of the phage or the target microorganism so detection of the epitope in a sample indicates that the protein comprising the epitope was produced by the microorganism following infection by the recombinant phage comprising a gene encoding the protein comprising the epitope. In other embodiments the marker may be a purification tag in the context of a protein that is naturally present in the target microorganism or the phage. For example, the tag (e.g., a 6-His tag [SEQ ID NO: 46]) can be used to purify the heterologous protein from other bacterial or phage proteins and the purified protein can then be detected, for example using an antibody.

In some embodiments the heterologous nucleic acid sequence comprises at least a first open reading frame and a second open reading frame. In some embodiments the first and second open reading frames are operatively linked to the same expression control sequences. In some embodiments the first and at least one second open reading frames are operatively linked to different expression control sequences.

In some embodiments the first open reading frame encodes a marker that confers at least one phenotype on a vector host cell comprising the vector selected from a selectable phenotype and a screenable phenotype, and the second open reading frame encodes a gene product that is not a marker that confers at least one phenotype on a vector host cell comprising the vector selected from a selectable phenotype and a screenable phenotype. In some embodiments the second open reading frame confers a phenotype of interest on a phage host cell expressing it.

One example of a heterologous nucleic acid cassette that may be used for homologous recombination to introduce a heterologous nucleic acid sequence into a cloned phage genome is a cassette comprising a first open reading frame encoding the selectable marker URA3 and a second open reading frame encoding luciferase. In this cassette the URA3 open reading frame encodes a marker that confers at least one phenotype on a vector host cell comprising the vector selected from a selectable phenotype and a screenable phenotype and the luciferase open reading frame encodes a protein that confers a phenotype of interest on a phage host cell comprising a phage genome comprising the open reading frame. In this case the luciferase gene product produces a detectable signal upon exposure to substrate luciferin and this signal in turn allows for detection of phage host cells infected by the engineered phage.

In some embodiments, all or part of a heterologous nucleic acid sequence present in a recombinant phage genome is deleted and/or replaced with a different heterologous nucleic acid sequence. The deletion and/or replacement may be performed, for example, in a vector host cell. In some embodiments a heterologous open reading frame is modified to encode a variant or mutein of the protein or polypeptide encoded by the starting open reading frame. In some embodiments this is accomplished using directed evolution.

In some embodiments the protein or polypeptide encoded by a heterologous open reading frame is modified to reduce cleavage by proteases present in phage host cells. For example, computational algorithms can be used to identify known protease cleavage sites and the sequence of the open reading frame can be modified using conservative substitutions to remove these sites. Alternatively, directed mutagenesis is used to evolve the open reading frame sequence to encode a product that has an increased resistance to at least one protease present in a phage host cell or in the culture of a phage host cell.

The heterologous open reading frame can also be supercharged to enhance its stability when expressed in a phage host cell.

In some embodiments the heterologous open reading frame comprises a sequence that encodes a polypeptide tag, such that the expression product of the open reading frame comprises the tag fused to a polypeptide or protein encoded by the open reading frame.

2. Selection of Sites for Insertion of Heterologous Nucleic Acid Sequences into Phage Genomes The expression of a heterologous open reading frame inserted into a phage genome will be influenced by many factors, including timing of expression in the phage lifecycle, promoter (transcriptional) strength, ribosome binding site (translational) strength, mRNA stability, protein degradation rates, codon usage, and others. Algorithms can be used to identify and predict sites within a phage genome that have desired expression properties.

Empirical algorithms are based on analysis of proteomics of natural phage protein expression both for at least one of temporal characteristics and absolute expression levels. For example, phage proteins can be tagged and expression levels monitored over time and/or under different conditions. Phage proteins exhibiting desirable expression traits are identified.

In some embodiments the phage protein is expressed at a relatively high level. In some embodiments the phage protein is expressed over a relatively long period of the phage lifecycle. In some embodiments the phage protein is a structural proteins such as a capsid component. Once a phage protein exhibiting a desirable expression trait is identified a heterologous nucleic acid sequence comprising an open reading frame is inserted into the phage genome to either replace the open reading frame encoding the identified protein or to place the open reading frame within the heterologous nucleic acid sequence downstream of the open reading frame of the protein exhibiting a desirable expression trait.

Computational algorithms are used to identify phage promoters within phage genomic sequences. One such algorithm is provided in Lavigne et al., Bioinformatics, Vol. 20, No. 5, pp. 629-635 (2004). Promoters that exhibit sequence homology to well-known promoters are particularly useful because it can be predicted that such promoters are likely to exhibit desirable functional characteristics. Ribosomal binding site (RBS) strength of endogenous phage genomic sequences can be estimated using the RBS Calculator available at https://salis.psu.edu/software/ (hereby incorporated herein by reference). RBS sequences predicted to have high efficiency are particularly be useful.

DNA sequence homology can also be used to identify open reading frames which are known to be expressed at high levels in other well-characterized phages (for example open reading frames of T7, T3, T4, and lambda phage). In some embodiments the heterologous nucleic acid sequence replaces such an open reading frame or is placed downstream of such an open reading frame. Lack of DNA sequence homology can be used to identify open reading frames that are non-essential and are more likely to tolerate insertions.

Many phages have similar genomic structures. Based on these genomic structures, sequence comparisons between a subject phage and a well-characterized phage is used to identify locations for insertion of the heterologous nucleic acid sequence into a subject phage. For example, there are early, middle, and late genes in T7-like phages which correspond to the temporal sequence in which they are expressed and correlated to position in the genome. Accordingly, homologous locations within a subject phage can be identified and a heterologous nucleic acid sequence inserted into an identified position.

Microarray experiments can identify which genes are turned on in early, middle and late stages of expression with little other information about the phage other than sequence. This is a quick method for getting a detailed expression profile of a novel phage.

The methods and vectors disclosed herein also make it feasible to test in parallel several different insertions into a phage genome experimentally. In some embodiments a plurality of insertion sites are tested to empirically identify insertion sites from which heterologous open reading frames are expressed with desirable characteristics. In some embodiments the insertion sites are random. In some embodiments the insertion sites are at predetermined locations. In some embodiments the tested insertion sites are a combination of at least one random insertion site and at least one predetermined insertion site.

In some embodiments a phage comprises a plurality of inserted heterologous nucleic acid sequences located at different sites within the phage genome. In some embodiments the inserted sequences are the same. In some embodiments the plurality of inserted heterologous sequences comprises at least two different heterologous sequences. In some embodiments the inserted heterologous sequences comprise open reading frames that are expressed at different levels at different stages of the phage lifecycle.

Phage lysis is a competing factor for expression of heterologous open reading frames inserted into a phage genome. If a phage kills a host cell too early, then open reading frame expression may not reach a desired level. The phage lifecycle can be altered to enhance heterologous open reading frame expression. For example, expression of lysis proteins (such as lysins and holins) can be reduced by altering their ribosome binding sequences to thereby extend the phage lifecycle and delay lysis. In some embodiments this process is used to increase at least one of total heterologous open reading frame expression during a phage lifecycle and maximum heterologous open reading frame expression during a phage lifecycle.

3. Insertion of Heterologous Sequences into Phage Genomes

Cloning of phage genomes in vectors that allow propagation in cells that are not phage-host cells, as demonstrated herein, enables application of several methods known in the art to insert heterologous nucleic acid sequences into the cloned phage genome present in the recombinant vector. The heterologous nucleic acid sequence may be inserted in vivo in a vector host cell (e.g., a yeast cell) or in vitro using a recombinant vector isolated from a vector host cell.

Random Via Transposon Hopping.

In one method, random delivery of a known piece of DNA via transposon hopping is used to deliver a heterologous nucleic acid sequence to random sites in a cloned phage genome. In some embodiments transposon insertion occurs in vivo. In some embodiments transposon insertion occurs in vitro. In some embodiments the transposon is used to deliver an open reading frame encoding a selectable marker to a site in the phage genome. The engineered phage genome may be further modified to comprise "handle" site comprising recognition sites for endonucleases in order to facilitate further genetic modification at the site.

Transposon delivery may provide random sampling of all the sites in the phage genome. After delivery of a transposon to a particular site in the phage genome, the resulting recombinant phage may be tested for viability (their ability to form phage particles) and optionally for at least one additional phage phenotype. In this way phage genomes comprising an inserted heterologous DNA may be screened to identify those having desirable characteristics. If the recombinant phage already carries a selectable marker this test simultaneously assays for the insertion site tolerating genetic change and also for the phage and the insertion site tolerating the size of inserted heterologous nucleic acid. Any insertion events that are tolerated are selected for, taking forward as sites for optional future genetic modification and transgene delivery.

Homologous Recombination

Homologous recombination may be used to insert a linear cassette into a cloned phage genome. In some embodiments the linear cassette comprises an open reading frame that encodes a selectable marker. In some embodiments the selectable marker confers at least one phenotype on a vector host cell comprising the phage genome selected from a selectable phenotype and a screenable phenotype. In such embodiments the selectable or screenable phenotype may be used to identify vector host cells that comprise a recombinant vector comprising the heterologous nucleic acid sequence. In some embodiments the heterologous nucleic acid sequence comprises an open reading frame that encodes a gene product that expresses a protein of interest in a phage host cell comprising a phage genome comprising the open reading frame. In some embodiments the selectable marker gene product and the gene product that expresses a protein of interest in a phage host cell comprising a phage genome comprising the open reading frame are the same. However, in several embodiments the selectable marker gene product and the gene product that expresses a protein of interest in a phage host cell comprising a phage genome comprising the open reading frame are different. In such embodiments the heterologous nucleic acid sequence comprises at least two open reading frames, a first open reading frame encoding the selectable marker and a second open reading frame encoding a gene product that expresses a protein of interest in a phage host cell comprising a phage genome comprising the open reading frame.

In some embodiments the recombinant phage genome is created in a YAC in a form comprising both first and second open reading frames. In some embodiments that recombinant phage genome is transferred to a phage host cell, as described below, such that the phage genome introduced into the phage host cell comprises both the first and second open reading frames. In some embodiments the first open reading frame that encodes the selectable marker that confers at least one phenotype on a vector host cell comprising the phage genome selected from a selectable phenotype and a screenable phenotype is removed from the recombinant phage genome before the recombinant phage genome is transferred to a phage host cell. For example, the open reading frame encoding the selectable marker may be removed from the recombinant phage genome using homologous recombination in yeast cells. Alternative methods such as Cre-loxP mediated recombination may also be used.

Homologous recombination in yeast is accomplished by creating a heterologous nucleic acid sequence comprising ends that are homologous to target sites in a cloned phage genome. If the heterologous nucleic acid sequence comprises an open reading frame encoding a selectable marker then insertion of the linear cassette into the phage-YAC may be selected for by plating on selective media (for example, media lacking uracil if the marker is URA3). The resulting phage-YACs will thus contain cassettes that comprise the selectable marker and thus the heterologous nucleic acid sequence. If the heterologous nucleic acid sequence comprises a second open reading frame that encodes a product that is not used for selection in yeast then this single selection also identifies recombinant phage-YACs comprising this second open reading frame.

Figure 3A:
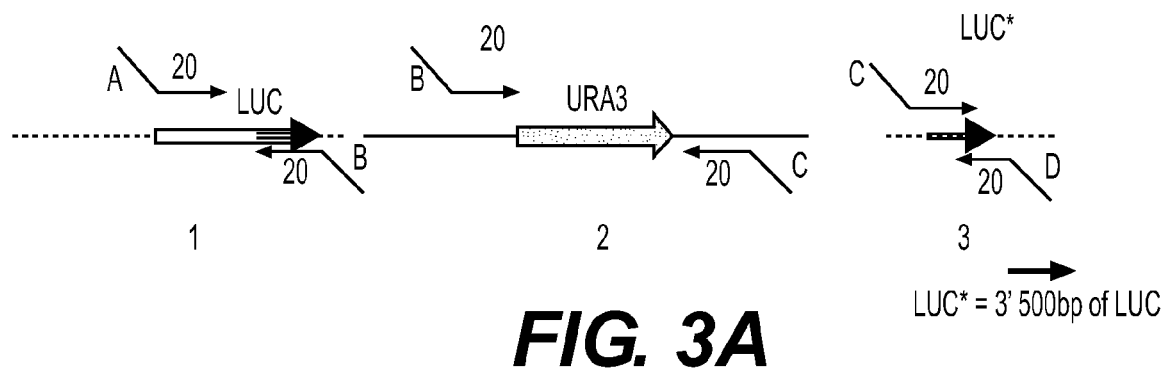
FIGS. 3A to 3E show an example of a cassette construct for insertion of the luciferase and Ura3 open reading frames into the T3 genome to replace either the 0.7 open reading frame or the 4.3 open reading frame (the alternative targets are both represented in the figure).
Figure 3B:
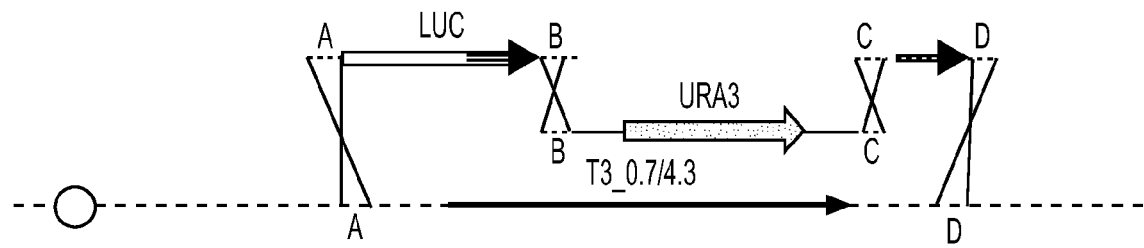
Figure 3C:
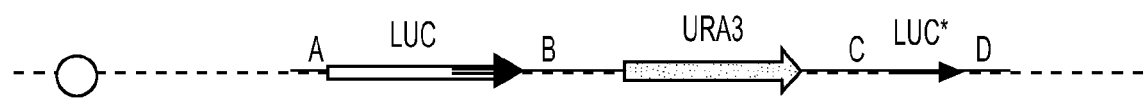
Figure 3D:
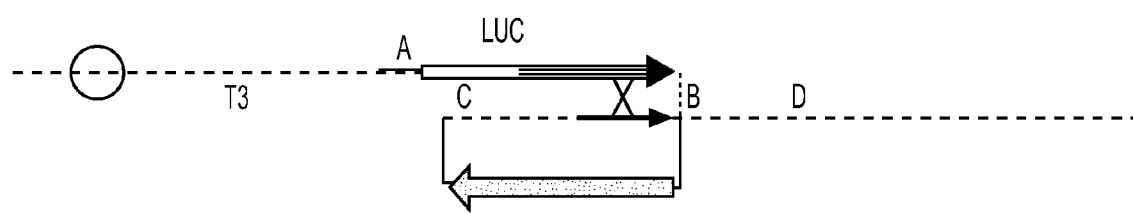
Figure 3E:
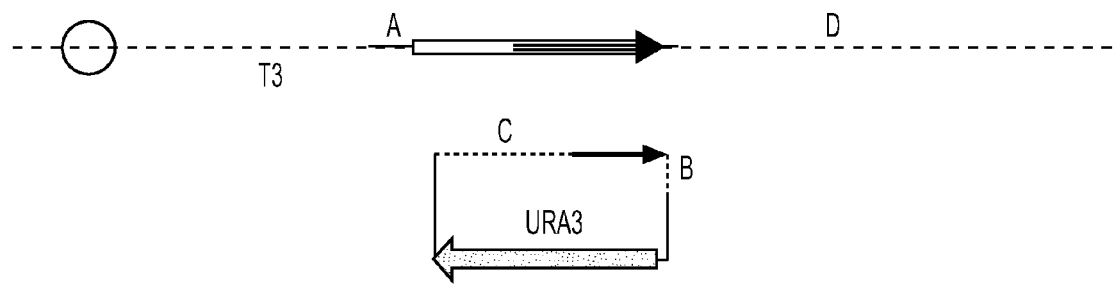

In some cases, removal of the selectable marker and extraneous sequences of the cassette are desirable. This may be achieved by engineering short direct repeats within the cassette; these direct repeats can be targeted by host recombination machinery resulting in the excision of the intervening DNA and selected for under appropriate culture conditions. An example of this strategy is shown in FIG. 3. The cassette structure is shown in FIG. 3A. From left to right, the cassette contains sequence elements A-Luc-B-URA3-C-Luc*-D, where Luc* is the 3' terminal end of the Luc gene and is thus homologous to the Luc gene located in between A and B. URA3 is a selectable marker (any suitable marker may be substituted for URA3). Insertion of this cassette by vector host cell recombination machinery into the phage genome is shown in FIG. 3B. This figure shows the general strategy used at the T3 0.7 and 4.3 genes as described in the Examples (labeled T3_0.7/4.3 in FIG. 3B). Following recombination the locus will have the structure shown in FIG. 3C. Vector host cells comprising the recombined vector may be selected on growth media lacking uracil.

Upon removal of selective pressure for the presence of the URA3 gene the host cells will recombine the homologous region shared by Luc and Luc*, resulting in phage-YACs which contain A-Luc-D only. If the selectable marker used is selectable and counterselectable (which URA3 for example is), then following selection of cells comprising the A-Luc-B-URA3-C-Luc*-D insertion using selection (for example, media without uracil), cells which have lost the selectable marker and thus are A-Luc-D through internal recombination (FIGS. 3D and 3E) may be counterselected (for example, by growth in media with 5'FOA when D is the URA gene). Variants of this strategy may be performed such that the scar DNA sequence remaining after the recombination is any arbitrary sequence.

4. Creating Phage Particles from Cloned Phage Genomes

Cloned phage genomes, whether genetically modified or not, may be used to create phage particles. If the cloned phage genome is a recombinant genome comprising a heterologous nucleic acid sequence the resultant phage particles will also be recombinant and in this way capable of transferring the recombinant heterologous sequence to phage host cells, which in turn may result in expression of a recombinant gene product encoded by the heterologous nucleic acid sequence in the phage host cells.

Choosing the method for converting engineered phage DNA constructs into viable phage particles is based on one or more of a variety of factors. For example, size limitations for bacterial host transformation may restrict the efficiency of direct transformation of engineered phage DNA constructs into host bacteria. The availability of highly competent strains for transformation as surrogate hosts may enable efficient delivery of phage DNA constructs into these surrogates prior to amplification on other susceptible hosts. In some embodiments the ability of bacterial types to perform homologous recombination on smaller DNA fragments to assemble longer DNA fragments allows for the transformation of smaller engineered phage DNA fragments into hosts followed by in-cell assembly back into functional phage genomes.

Direct Transformation.

The examples herein demonstrate transformation of engineered phage genomes directly as phage-YAC DNA into an appropriate host cell. These phage-YACs replicate, excise and package into infectious phage particles capable of repeated infection.

In this method, engineered YACs are recovered from yeast transformants comprising the YACs. In some embodiments this is accomplished by disrupting the yeast transformant by glass bead lysis thereby releasing the YACs from the transformed cells. The released YACs bearing phage are electroporated into an appropriate phage host cell and plated in a standard plaque assay. The inventors have produced plaques from a transformation of YACs bearing phage genomes. To date this has been successfully accomplished using *E. coli* phages (T3 and T7) and *Salmonella* phage (FelixO1). These results demonstrate production of functional phage from cloned phage genomes.

Liberation of Phage DNA, Followed by Direct Transformation.

Not all phages will tolerate the presence of foreign DNA at a terminus. To mitigate this, linearization of vectors to remove the exogenous DNA and liberate phage genomic DNA is used to improve transformation efficiency. To that end, in some embodiments cloning vectors designed to allow flush cutting of the vector to liberate phage DNA that recapitulates the original phage genome are used. In some embodiments the cloning vectors are created to comprise meganuclease recognition sites for this purpose. Further protection of ends by incubating this DNA with phage extracts, for example, allows protection of the ends to improve transformation efficiency.

Circularization.

Some phage genomes require a circularized state to produce viable phage particles in host bacteria. Accordingly, in some embodiments plasmids comprising a phage genome surrounded by recombinase recognition sites are used. Upon expression of the recombinase, either in bacteria, yeast, or in vitro, the phage genome is circularized, creating a genome structure that supports production of viable phages.

Alternatively, phage genomes are excised from vectors using restriction enzymes to digest DNA at or near their ends and then circularized using DNA ligase.

Surrogate Transformation.

Phage host-range is often determined by the presence or absence of receptors on the surface of the cell. Closely related organisms that use largely the same replication, transcription and translation machinery may actually be cross-resistant to different phages due to external cell-surface factors. In addition, some bacterial hosts are easier to transform than others. In view of this, genetically tractable, related bacterial strains may be used to make phage bursts from engineered phage DNA constructs. Accordingly, in some embodiments, the cloned phage genomic DNA is transformed into a surrogate strain, recovered after a period of time, and then the phage lysate is exposed to a sensitive host for propagation of the lysate into a higher titer lysate. In this way surrogate transformation (also called trans-transformation) allows recovery of phages from hosts that are otherwise un-transformable.

For example, an engineered *Salmonella* phage DNA construct may be transformed into *E. coli* efficiently due to its high transformation efficiency, the resulting lysate collected and used to infect *Salmonella* host cells for subsequent phage propagation. This was done for *Salmonella* phage of Felix01. An infectious lysate was obtained after grow out of culture that had been electroporated with phage-YAC DNA into *E. coli*.

This method may be used with gram-negative surrogates and gram-negative hosts, gram-negative surrogates and gram-positive hosts, gram-positive surrogates and gram-positive hosts, and gram-positive surrogates and gram-negative hosts.

Surrogate Transformation Followed by Conjugation.

An alternate to transformation of engineered phage DNA into a surrogate host bacteria followed by bursting and amplification on a different susceptible host strain ("Surrogate transformation" as described above), is the transformation of engineered phage DNA into a surrogate host bacteria followed by conjugation of the engineered phage DNA construct into a different susceptible host strain. This method is useful for engineering phages which have difficult-to-transform hosts. For example, a gram-positive bacterial host may be difficult to directly transform with an engineered phage DNA construct. In this case, the phage DNA construct in a vector that contains conjugation machinery is transformed into a surrogate bacterial strain (such as *E. coli*) which is then capable of conjugating the phage DNA construct into a different susceptible host strain (such as the gram-positive host of the phage).

5. Verifying Engineered Phages

Recombinant phage made or derived from a cloned phage genome may be characterized in a number of ways. The genome structure of such phage may be characterized using PCR screening, restriction digestion, sequencing, or a combination thereof. For example, primers that flank the desired insertion site of the heterologous nucleic acid sequence in the phage genome may be designed and used to identify the presence of the heterologous nucleic acid sequence based on successful PCR amplification of the fragment. qPCR primers can also be used to detect the presence of genetic changes such as insertions, deletions, or substitutions. Purified phage genomic DNA from viable phage particles can be purified and subjected to restriction digestion and analysis to confirm genomic structure. Direct sequencing may also be used to provide a high resolution of genome structure.

Phenotypic screening may also be used to characterize recombinant phage particles. In some embodiments recombinant phage and libraries of recombinant phage are screened to identify phenotypes of interest. In some embodiments phenotypic screening is used directly as an assay for recombinant phage of interest. For example, screening biofilm removal or bacterial detection.

In some embodiments enzyme assays for the expression products of the heterologous nucleic acid sequences present in the recombinant phage give a good indication of optimal phage properties. For example, phages with high levels of luciferase expression or high levels of xylanase expression to remove xylans from biofilm matrix.

In some embodiments competition experiments identify phages that carry properties of interest, optionally including selected growth characteristics. Mixing phages together, and recovering the dominant phages at the end of a mixed infection is used in some embodiments to identify phages that carry a combination of properties of interest.

D. Methods of Making Collections of Engineered Phages and Collections of Engineered Phages The methods disclosed herein allow for high throughput generation of diverse collections of recombinant phage. The collections may be designed to include at least one of a plurality of different starting phage genomes, a plurality of inserted heterologous nucleic acid sequences, and a plurality of different insertions sites of the heterologous nucleic acid sequences into a starting phage genome.

In some embodiments the plurality of recombinant vectors comprises a plurality of different heterologous nucleic acid sequences. The heterologous nucleic acid sequences may differ in one or more ways. For example, the heterologous nucleic acid sequences may comprise different open reading frames that include different products. Alternatively or in addition the heterologous nucleic acid sequences may comprise different expression control sequences that direct expression of an open reading frame in a different manner, such as at a different maximum level of expression or in a different temporal profile during a phage infection lifecycle. For example, the expression control sequences may differ in promoter or ribosome binding site. The heterologous nucleic acid sequences may also differ in length or nucleotide composition. In some embodiments the plurality of heterologous insertion sequences consist of sequences that each differ from every other sequence by at least 1%, at last 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, or at least 50% at the nucleotide level. In some embodiments the plurality of heterologous insertion sequences consist of sequences that comprise open reading frames, and the open reading frames each differ from every other open reading frame sequence by at least 1%, at last 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, or at least 50% at the nucleotide level. In some embodiments the plurality of heterologous insertion sequences consist of sequences that comprise open reading frames, and the open reading frames encode products that each differ from every other open reading frame encoded product by at least 1%, at last 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, or at least 50% at the amino acid level.

In some embodiments the plurality of recombinant vectors comprises a plurality of different heterologous nucleic acid sequences and at least 5 different heterologous nucleic acid sequences are present in the plurality of recombinant vectors. In some embodiments at least 10, at least 15, at least 20, at least 25, at least 30, at least 35, at least 40, at least 45, at least 50, at least 60, at least 70, at least 75, at least 80, at least 85, at least 90, at least 95, at least 100, at least 200, at least 300, at least 400, or at least 500 different heterologous nucleic acid sequences are present in the plurality of recombinant phage vectors.

In some embodiments the plurality of recombinant vectors comprises at least two types of recombinant phage genomes, in which the heterologous nucleic acid sequence is inserted at different locations. In some embodiments the recombinant phage genomes present in the plurality of vectors are based on the same starting phage genome. Thus, in such embodiments the heterologous sequence is inserted at different sites in the same phage genome. In other embodiments the recombinant phage genomes present in the plurality of vectors are based on at least two different starting phage genomes.

In some embodiments the plurality of recombinant phage genomes comprises at least 5 types of recombinant phage genomes, in which the heterologous nucleic acid sequence is inserted at different locations. In some embodiments the plurality of recombinant phage genomes comprises at least 10, at least 15, at least 20, at least 25, at least 30, at least 35, at least 40, at least 45, at least 50, at least 60, at least 70, at least 75, at least 80, at least 85, at least 90, at least 95, at least 100, at least 200, at least 300, at least 400, or at least 500 types of recombinant phage genomes, in which the heterologous nucleic acid sequence is inserted at different locations.

In some embodiments the plurality of recombinant vectors comprises a common first open reading frame and a plurality of different second open reading frames, and at least 5 different second open reading frames are present in the plurality of recombinant vectors. In some embodiments at least 10, at least 15, at least 20, at least 25, at least 30, at least 35, at least 40, at least 45, at least 50, at least 60, at least 70, at least 75, at least 80, at least 85, at least 90, at least 95, at least 100, at least 200, at least 300, at least 400, or at least 500 different second open reading frames are present in the plurality of recombinant phage vectors Collections of recombinant phage genomes and/or recombinant phage comprising the recombinant genomes are also provided. The collections include recombinant phage genomes and phages with recombinant genomes that include at least one starting phage genome, at least one heterologous insertion sequence, and at least one site of insertion of the at least one heterologous insertion sequence in the at least one starting genome. In some embodiments the collection includes at least 2, 3, 4, 5, 6, 7, 8, 9, 10, 20, 30, 40, 50, 60, 70, 80, 90, 100, 500, or 1000 different types of starting phage genome. In some embodiments the collection includes at least 2, 3, 4, 5, 6, 7, 8, 9, 10, 20, 30, 40, 50, 60, 70, 80, 90, 100, 500, or 1000 different types of heterologous insertion sequence. In some embodiments the collection includes at least 2, 3, 4, 5, 6, 7, 8, 9, 10, 20, 30, 40, 50, 60, 70, 80, 90, 100, 500, or 1000 different sites of insertion of the at least one heterologous insertion sequence in the at least one starting genome. Thus, in some embodiments of the collection a single heterologous insertion sequence is inserted at least 2, 3, 4, 5, 6, 7, 8, 9, 10, 20, 30, 40, 50, 60, 70, 80, 90, 100, 500, or 1000 different sites in the same starting phage genome. In other embodiments more than one heterologous insertion sequence is present in the collection and/or more than one starting phage genome is present, and there are at least 2, 3, 4, 5, 6, 7, 8, 9, 10, 20, 30, 40, 50, 60, 70, 80, 90, 100, 500, or 1000 different sites of insertion of the heterologous nucleic acid sequence into phage genomes present in the collection.

In some embodiments the collection of recombinant phage genomes are not packaged into phage particles. For example, in some embodiments the collection of recombinant phage genomes are present in vectors, such as YACs. In some embodiments the vectors are stored in isolated or purified form. In other embodiments the vectors are present in vector host cells, such as yeast, which can be in any form such as a frozen glycerol stock or growing on solid or liquid media.

In some embodiments the collection of recombinant phage genomes are packaged into phage particles.

In some embodiments all or substantially all members of the collection are present together in a mixture, such as a liquid culture that contains phage particles or a liquid culture that contains a library of different yeast cells. In other embodiments all or substantially all members of the collection are stored isolated from one and other, such as in different cultures or as different frozen glycerol stocks.

In some embodiments a collection of phage or phage chromosomes is screened to identify a subset of the collection that shares one or more features. For example, if the collection comprises phage genomes from different starting phage the collection may be screened to identify members of the collection that are capable of infecting a particular type or combination of types of bacteria. Alternatively, the collection may be screened to identify members of the collection that express heterologous open reading frame products above a certain level.

EXAMPLES

The following examples serve to more fully describe the manner of using the invention. These examples are presented for illustrative purposes and should not serve to limit the true scope of the invention.

Example 1

Cloning and Genetically Modifying Phage T3

A. Phage Capture

Phage T3 was cloned and manipulated in the following manner. T3 was grown using *E. coli* DH10B as a host, grown in Luria Broth (LB)+2 mM calcium chloride. The phage lysate was concentrated via incubation with 10% polyethylene glycol-8000 overnight at 4° C., followed by centrifugation. The pellet was resuspended in SM buffer (Sambrook et al., Molecular Cloning: A Laboratory Manual, 3d ed., Cold Spring Harbor Laboratory Press, Cold Spring Harbor, N.Y. (2001)). DNA was prepared from the concentrated T3 lysate using the Norgen Phage DNA kit (Cat#46700). The genomic sequence of T3 (NCBI accession #NC_003298) was used to design oligos to capture T3 into the pYES1L vector (Invitrogen®). Oligos used were duplexes of:

```
                                              [SEQ ID NO: 1]
CCTAGTGTACCAGTATGATAGTACATCTCTATGTGTCCCTCCTCGCCGCA

GTTAATTAAAGTCAGTGAGCGAGGAAGCGC
and its complement,
``` and duplexes of:

[SEQ ID NO: 2]
GAACGACCGAGCGCAGCGGCGGCCGCGCTGATACCGCCGCTCTCATAGTT

CAAGAACCCAAAGTACCCCCCCCATAGCCC
and its complement.

The oligos were transformed into competent MaV203 yeast cells (Invitrogen®) together with purified T3 DNA and yeast artificial chromosome pYES1L Transformed cells were plated on synthetic complete media without tryptophan, selecting for the TRP marker on pYES1L. Colonies that grew on synthetic complete trp-minus were screened by PCR to show successful capture of the T3 genome.

B. YAC to Plaque

Selected MaV203 cells that contained the pYES1L-T3 phage-YAC were grown up and glass-bead lysates were prepared (Invitrogen® High-Order Genetic Assembly kit) and electroporated into TOP10 *E. coli*. The transformations were mixed with LB+2 mM calcium chloride top agar, and plated on an LB+2 mM calcium chloride agar plate. Incubations overnight revealed plaques, corresponding to the captured phage. Captured phages typically yielded $1 \times 10^2$ to $1 \times 10^4$ plaques per transformation.

C. Luciferase Insertion into Cloned T3 Phage

Expression cassettes were designed for insertion into different locations of the T3 genome. The cassettes contain an intact luciferase open reading frame inserted to take the place of an endogenous T3 gene such that luciferase expression is driven by the endogenous T3 promoter, followed by the URA3 gene with its own promoter, and optionally a direct repeat of the 3' end of the luciferase gene. Insertions were made into the T3 0.7 and 4.3 genes. In T3::0.7 luc a cassette containing luciferase and URA3 is swapped into the T3 0.7 gene. In T3::0.7DRluc a cassette containing luciferase, URA3, and a direct repeat of the 3' end of the luciferase gene is swapped into the T3 0.7 gene. In T3::4.3DRluc a cassette containing luciferase, URA3, and a direct repeat of the 3' end of the luciferase gene is swapped into the T3 4.3 gene. In T3::0.7IceuILuc a cassette containing luciferase, URA3, and a ICeu I homing endonuclease site is swapped into the T3 0.7 gene.

For insertion, the cassettes were amplified as two or three PCR products, one containing the luciferase and flanking homology to a first site in the phage, the second containing the URA3 gene with flanking homology to the other two PCR products, and the third containing a fragment of luciferase, and homology to a different site on the phage chromosome. The constructs were designed to replace the targeted gene without deleting other adjacent sequences. The internal fragment containing URA3 was amplified using primers:

[SEQ ID NO: 3]
CCTCATAAAGGCCAAGAAGGGCGGAAAGTCCAAATTGTAAACGGATTCAC

CACTCCAAGA
and

[SEQ ID NO: 4]
ATAATCATAGGTCCTCTGACACATAATTCGCCTCTCTGATTCAACGACAG

GAGCACGATC.

The 3' end of the full luciferase fragment was amplified by:

[SEQ ID NO: 5]
AAGAATTGATTGGCTCCAATTCTTGGAGTGGTGAATCCGTTTACAATTTG

GACTTTCCGC.

The 5' end of the shorter luciferase fragment was amplified by:

[SEQ ID NO: 6]
TCCTGGCCACGGGTGCGCATGATCGTGCTCCTGTCGTTGAATCAGAGAGG

CGAATTATGT.

For inserting this duplication cassette at the T3 0.7 gene, the 5' end of the full luciferase fragment was amplified with:

[SEQ ID NO: 7]
AATTTACTCTTTACTCTTACAGATAACAGGACACTGAACGATGGAAGACG

CCAAAAACAT, and the 3' end of the shorter luciferase fragment with:

[SEQ ID NO: 8]
ATTCAGGCCACCTCATGATGACCTGTAAGAAAAGACTCTATTACAATTTG

GACTTTCCGC.

For insertions at the 4.3 gene site, the 5' end of the full luciferase fragment was amplified with:

[SEQ ID NO: 9]
CTCACTAACGGGAACAACCTCAAACCATAGGAGACACATCATGGAAGACG

CCAAAAACAT, and the 3' end of the shorter luciferase fragment with

[SEQ ID NO: 10]
TGTTTGCGTGCTTGATTGATTTACTCATGTTGTGCTCCTATTACAATTTG

GACTTTCCGC.

In each case (0.7 and 4.3 gene sites), 3 PCR products were created, and co-transformed into yeast containing the T3-YAC described above. Recombination was selected by growing cells in the absence of uracil. Colonies that grew in the absence of uracil were screened by PCR for presence of the cassette. Colonies positive by PCR were subjected to the YAC-to-plaque technique (described above) to recover viable phages. These phages were subsequently screened by PCR to confirm the presence of the cassette.

D. Expression of Luciferase in Recombinant Phage

An overnight culture of *E. coli* cells was diluted 1/100 and grown into mid-log phase in LB+1 mM calcium chloride (approximately 2 and a half hours). Cells were diluted and infected with a vast excess of phages ($1 \times 10^7$ phages per infection) in a total of 100 ul. Infections were allowed to proceed, non-shaking at 37 degrees C. After 90 minutes, 100 ul of Promega® Steady-Glo luciferase detection reagent was added to 20 uL of infection, and infections were immediately read on a Promega® GloMax 20/20. Cells infected with the different engineered phage showed some variation of expression levels, but cells infected with T3::0.7Luc, T3::DRLuc, T3::4.3DRLuc, and T3::0.7IceuILuc all expressed detectable levels of luciferase.

Example 2

Cloning and Genetically Modifying Phage T7

A. Phage Capture

T7 luc was created in a slightly different manner than the engineered T3 phage of Example 1.

T7 dspB (T. K. Lu and J. J. Collins, "Dispersing Biofilms with Engineered Enzymatic Bacteriophage," Proceedings of the National Academy of Sciences, vol. 104, no. 27, pp. 11197-11202, Jul. 3, 2007, incorporated herein by reference) was captured in pYES1L by transforming genomic DNA of T7 dspB, YAC pYES1L, a duplex of:

[SEQ ID NO: 11]
TTGTCTTTGGGTGTTACCTTGAGTGTCTCTCTGTGTCCCTCCTCGCCGC

AGTTAATTAAAGTCAGTGAGCGAGGAAGCGC and its complement, and a duplex of:

[SEQ ID NO: 12]
CCCGAACGACCGAGCGCAGCGGCGGCCGCGCTGATACCGCCGCCGCCGG

CGTCTCACAGTGTACGGACCTAAAGTTCCCCCATAGGGGGT and its complement,
into MaV203 yeast cells (Invitrogen®). Those oligonucleotides bridge the ends of the T7 genomic sequence (NC_001604) and the YAC vector.

B. YAC to Plaque

Cloned T7 phages were shown to be able to YAC-to-plaque, as above.

Selected MaV203 cells that contained the pYES1L-T7 dspB phage-YAC were grown up and glass-bead lysates were prepared (Invitrogen® High-Order Genetic Assembly kit) and electroporated into TOP10 *E. coli*. The transformations were plated and overnight incubations revealed plaques, corresponding to the captured phage.

C. Luciferase Insertion into Cloned T7 Phage

The T7-dspB YAC was purified by glass-bead lysate, and cut with EcoRI and HindIII. Luciferase was amplified with the primers

[SEQ ID NO: 13]
TAGAAATAATTTTGTTTAACTTTAAGAAGGAGATATACATATGGAAGAC

GCCAAAAACAT
and

[SEQ ID NO: 14]
CCAAGGGGTTAACTAGTTACTCGAGTGCGGCCGCAAGCTTTTACAATTT

GGACTTTCCGC.

Duplexed

[SEQ ID NO: 15]
ACATTTTCTGGCGTCAGTCCACCAGCTAACATAAAATGTAAGCTTTCGG

GGCTCTCTTGCCTTCCAACCCAGTCAGAAAT and its complement was also used to repair the HindIII cut YAC backbone. The cut phage-YAC, luciferase PCR product and duplexed repair oligos were co-transformed into MaV203 yeast cells (Invitrogen®), and selected on media lacking tryptophan, resulting in a single TRP+ colony. Engineered phage-YAC were confirmed by PCR and converted into phage particles via the YAC-to-plaque technique, as described above.

D. Expression of Luciferase in *E. Coli* Infected with Recombinant Phage

An overnight culture of *E. coli* cells was diluted 1/100 and grown into mid-log phase in LB+1 mM calcium chloride (approximately 2 and a half hours). Cells were diluted and infected with a vast excess of phages ($1 \times 10^7$ phages per infection) in a total of 100 ul. Infections were allowed to proceed, non-shaking at 37 degrees C. After 90 minutes, 100 ul of Promega® Steady-Glo luciferase detection reagent was added to 20 uL of infection, and infections were immediately read on a Promega® GloMax 20/20. Cells infected with the T7::Luc phage expressed of detectable levels of luciferase.

Example 3

Cloning and Genetically Modifying Phage T3

Phage T3 was captured into the pYES1L vector (Invitrogen®) and shown to be functional in the YAC to plaque assay as described in Example 1.

A. Luciferase and Nanoluc Insertion into T3 Phage

The T3 luciferase cassette was constructed as in Example 1.

Promega® vector pNL1.1 was the template for amplification of the nanoluc ORF with primers JHONO319 and JHONO320. pRS426 was used as a template for the Ura3 gene with primers JHNO321 and JHONO322. The sequences of those primers are:

JHONO319
[SEQ ID NO: 16]
AATTTACTCTTTACTCTTACAGATAACAGGACACTGAACGATGGTCTTC

ACACTCGAAGA

JHONO320
[SEQ ID NO: 17]
TTACGCCAGAATGCGTTCGCAC

JHONO321
[SEQ ID NO: 18]
AGTGACCGGCTGGCGGCTGTGCGAACGCATTCTGGCGTAACAGATTGTA

CTGAGAGTGCACC

JHONO322
[SEQ ID NO: 19]
ATTCAGGCCACCTCATGATGACCTGTAAGAAAAGACTCTACACACCGCA

TAGGGTAATAACTG.

In each case (luc cassette and nanoluc cassette), 2 PCR products were created, and co-transformed into yeast containing the T3-YAC described above in Example 1. Recombination was selected by growing cells in the absence of uracil. Colonies that grew in the absence of uracil were screened by PCR for presence of the cassette. Colonies positive by PCR were subjected to the YAC-to-plaque technique (described above) to recover viable phages. These phages were subsequently screened by PCR to confirm the presence of the cassette. Note that for these cassettes the URA3 gene was not excised.

Figure 4:
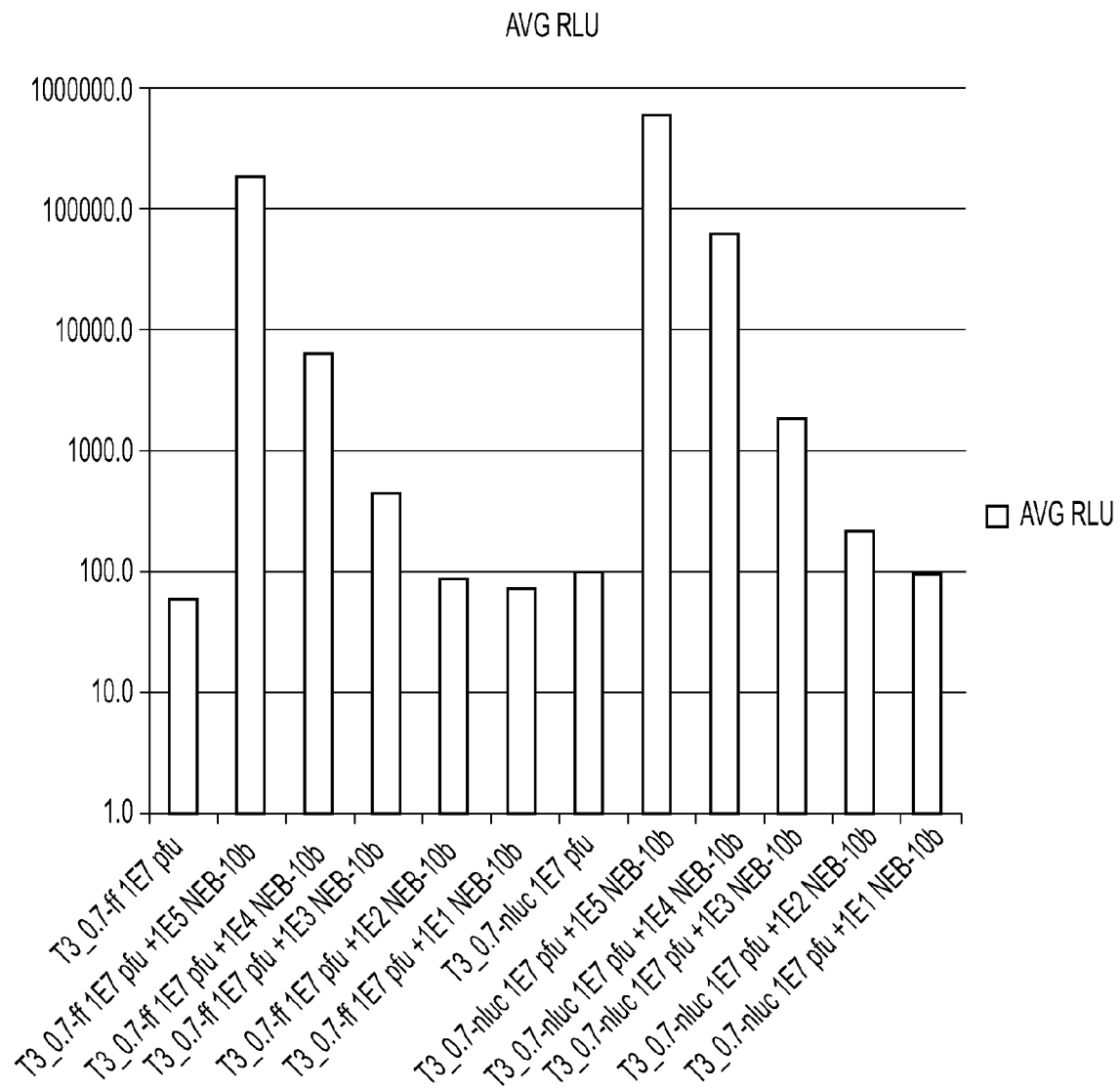
FIG. 4 shows the relative luminescence units generated when a fixed amount of engineered T3 phage comprising heterologous luciferase or nanoluc open reading frames was used to infect *E. coli* NEB10 cells.

B. Expression of Luciferase and Nanoluc in *E. Coli* Infected with Recombinant Phage Replacement of the T3 0.7 gene with the luc and nano luc cassettes allowed for quantitative comparison of the two open reading frames. The titer of luciferase expression phage was determined and a dilution series of NEB-10b cells was then infected with the same number of infective bacteriophage. This strategy allows for a direct comparison of the activity of the luc and nanoluc open reading frames. FIG. 4 reports the results of this experiment as relative luminescence units/number of infective phage (RLU/PFU). This data shows that the nanoluc ORF produces a higher ratio of RLU/PFU than the luc cassette.

Example 4

Cloning and Genetically Modifying Felix Phage

A. Phage Capture

Felix was grown using *Salmonella* LT2 as a host, grown in LB+2 mM CaCl2_. A phage lysate was prepared and concentrated via NaCl/PEG precipitation/cesium chloride gradient The genomic sequence of Felix was used to design capture oligos to capture Felix into the pYES1L vector (Invitrogen®). Oligos used were duplexes of
DBONO184

[SEQ ID NO: 20]
GAGTTCAACTTCTTTGGAGACATCTCAAGCACAGATTACAGATCCACTA

GTTCTAGAGCGGCCGCCACCGCGGTGGAGCT and its compliment and
DBONO185

[SEQ ID NO: 21]
AGCGCGCGTAATACGACTCACTATAGGGCGAATTGGGTACATGACACCT

GAAATGTTCAGCCTTCTGAGTTCTGGTGTAT and its complement.

The oligos were transformed into competent MaV203 yeast cells (Invitrogen®) together with purified Felix DNA and yeast artificial chromosome pRS414. Transformed cells were plated on synthetic complete media without tryptophan, selecting for the TRP marker on pYES1L. Colonies that grew on synthetic complete trp-minus media were screened by PCR and DNA sequencing to show successful capture of the Felix genome.

B. YAC to Plaque

Strains bearing Felix01 Phage_YACs were unable to support phage production in *Salmonella enterica* serovar *Typhimirium* LT2 cells (ATCC 19585) using the standard YAC to plaque assay described in the preceding examples. However, electroporation of the Felix01_phage YAC into NEB-10b cells generated a lysate that contained infectious Felix01 bacteriophage that were then used to form plaques in an infection of *Salmonella enterica* serovar Typhimirium LT2 (ATCC 19585). This process has been called surrogate transformation and in this case allowed for derivation of cloned engineered Felix01 phage capable of infecting host *Salmonella enterica* serovar *Typhimirium* LT2 (ATCC 19585) cells.

C. Luciferase Insertion into Cloned Felix Phage

Expression cassettes were designed for insertion into different locations of the Felix genome. For insertion, the cassettes were amplified as three PCR products, one containing the luciferase and flanking homology to a first site in the phage, the second containing the URA3 gene with flanking homology to the other two PCR products, and the third containing a fragment of luciferase, and homology to a different site on the phage chromosome. The internal fragment containing URA3 was amplified using primers:

[SEQ ID NO: 3]
CCTCATAAAGGCCAAGAAGGGCGGAAAGTCCAAATTGTAAACGGATTCA

CCACTCCAAGA
and

[SEQ ID NO: 4]
ATAATCATAGGTCCTCTGACACATAATTCGCCTCTCTGATTCAACGACA

GGAGCACGATC.

The 3' end of the full luciferase fragment was amplified by:

[SEQ ID NO: 5]
AAGAATTGATTGGCTCCAATTCTTGGAGTGGTGAATCCGTTTACAATTT

GGACTTTCCGC.

The 5' end of the shorter luciferase fragment was amplified by:

[SEQ ID NO: 6]
TCCTGGCCACGGGTGCGCATGATCGTGCTCCTGTCGTTGAATCAGAGAG

GCGAATTATGT.

The 5' end of luciferase and the 3' end of the truncated luciferase (luc*) contain sequences specific for the targeted locus for integration. In the case of Felix 01 (NCBI accession NC_005282) integration gene cassettes were made to target the following loci of the Felix01 genome: GP37, ORF51, ORF83, ORF19, ORF23, ORF46, ORF83. For ORF51, ORF83, ORF19, ORF23, ORF46, and ORF83 the cassette replaced the endogenous open reading frame. GP37 is a tail fiber gene and for it the insertion was at a downstream location and included an introduced Shine-Dalgarno sequence upstream of luciferase.

The locus-specific oligonucleotides used to amplify the 5' luciferase (F) and 3' luciferase* (R) are:

GP37

[SEQ ID NO: 22]
(F)-TTCTATAAGCTGATGGCTTGGGTAAGAACTGCTTAATCCCAGGAA

ACAGGATCCAAATGGAAGACGCCAAAAACAT

[SEQ ID NO: 23]
(R)-CATAAAGAATATTAACACCATCTTAACAATCAGTCAATAATTACA

ATTTGGACTTTCCGC

ORF51

[SEQ ID NO: 24]
(F)-TTTTAAGGGGAAACGAGATTTATTATTTGGAGAAAACATAATGGA

AGACGCCAAAAACAT

[SEQ ID NO: 25]
(R)-TAACAGCATTTAAGTCCATTAAGCGCCTCCGCAAATAGAATTACA

ATTTGGACTTTCCGC

ORF83

[SEQ ID NO: 26]
(F)-GATGACATCAAGTGTCTGTTCCCATAATAGGTGATTAACTATGGA

AGACGCCAAAAACAT

[SEQ ID NO: 27]
(R)-TAGGTGTTCCATCAGACTCATAGCAGTGTTCAATTTTCATTTACA

ATTTGGACTTTCCGC

ORF19

[SEQ ID NO: 28]
(F)-GGTTTTTAGATAGATTAAATTACACATCAACGGGGAGGGAATGGA

AGACGCCAAAAACAT

[SEQ ID NO: 29]
(R)-GGGCTTACTTTACAGACTTTTAAGCCCCATGTAAAGCACTTTACA

ATTTGGACTTTCCGC

-continued

ORF23

[SEQ ID NO: 30]
(F)-CTCCCCACTAAATAAAACCCTTAAACTAGGAGATTCTAAAATGGA

AGACGCCAAAAACAT

[SEQ ID NO: 31]
(R)-CTGTTAGGGTATCTGGGGCTATTTAGCCCCGCTGCGTCGATTACA

ATTTGGACTTTCCGC

ORF46

[SEQ ID NO: 32]
(F)-GCCAAACTGTCTTGAAAACAGTTGCCACTGTAGAGATACGATGGA

AGACGCCAAAAACAT

[SEQ ID NO: 33]
(R)-ACAACAAGCGGTAATAACCTTAGAAGCCCTCTAAAAAGACTTACA

ATTTGGACTTTCCGC

ORF83

[SEQ ID NO: 34]
(F)-GATGACATCAAGTGTCTGTTCCCATAATAGGTGATTAACTATGGA

AGACGCCAAAAACAT

[SEQ ID NO: 35]
(R)-TAGGTGTTCCATCAGACTCATAGCAGTGTTCAATTTTCATTTACA

ATTTGGACTTTCCGC.

Recombinants for luciferase cassette integrations at the target loci were confirmed with junctional PCR spanning the recombinant junctions. Sequencing of those PCR products revealed the desired integrations had occurred.

Surrogate transformations of the engineered Felix 01 phage into NEB-10b cells were attempted as described previously. Many of these transformations resulted in plaques, of the starting wild-type Felix 01 phage. PCR primer combinations that could amplify either a recombinant YAC or a wild-type Felix01 YAC detected both products in many clones. This result suggested the presence of a heterogeneous population of cells. Streaking of cells on ura-minus, leu-minus plates yielded single colonies of mixed genotype. As an alternative strategy, genomic DNA was isolated from these cells and re-transformed into yeast (haploid and diploid). No re-transformants were obtained.

Without wishing to be bound by any particular theory, these data suggest the possibility that there may be an extra, wild-type phage YAC present in the cells that will not segregate away under selection. This could occur, for example, if the diploid host cells maintain multiple copies of the plasmid.

Another possible explanation is that the increase in genome size resulting from adding ~3 kb to the phage genome causes problems in phage DNA packaging. Some phages are unable to tolerate increases in genome size this large and Felix 01 may be such a phage. In that regard it is noteworthy that the engineering platform developed herein allows for quick and easy testing of the tolerance of any phage to the addition of DNA to its genome. The high throughput enabled by this disclosure allows for screening of large numbers of phage in parallel and selection of those with any desired property or properties. That approach may be used to select one or a set of phage amenable to engineering.

With respect to engineering Felix 01, one option is to use a haploid strain to capture Felix 01. If the diploid genome of the strain that was used in the impediment then this will allow isolation of pure engineered phage YACs, leading to engineered phages via surrogate transformation.

If the genome size is the impediment, an alternative strategy is to remove portions of the Felix 01 genome that are not necessary for phage replication and thereby reduce the net addition of DNA to the Felix 01 genome.

Example 4

Cloning A511 Phage

A511 is a phage that specifically infects *Listeria* cells. The A511 genome (NC_009811) is 137,619 nucleotides long and characterized by a 3125 bp terminal repeat. The A511 genome was captured using YAC pRS415, linearized with BamHI and XhoI and treated with NEBNext end repair module (New England Biolabs).

Figure 2:
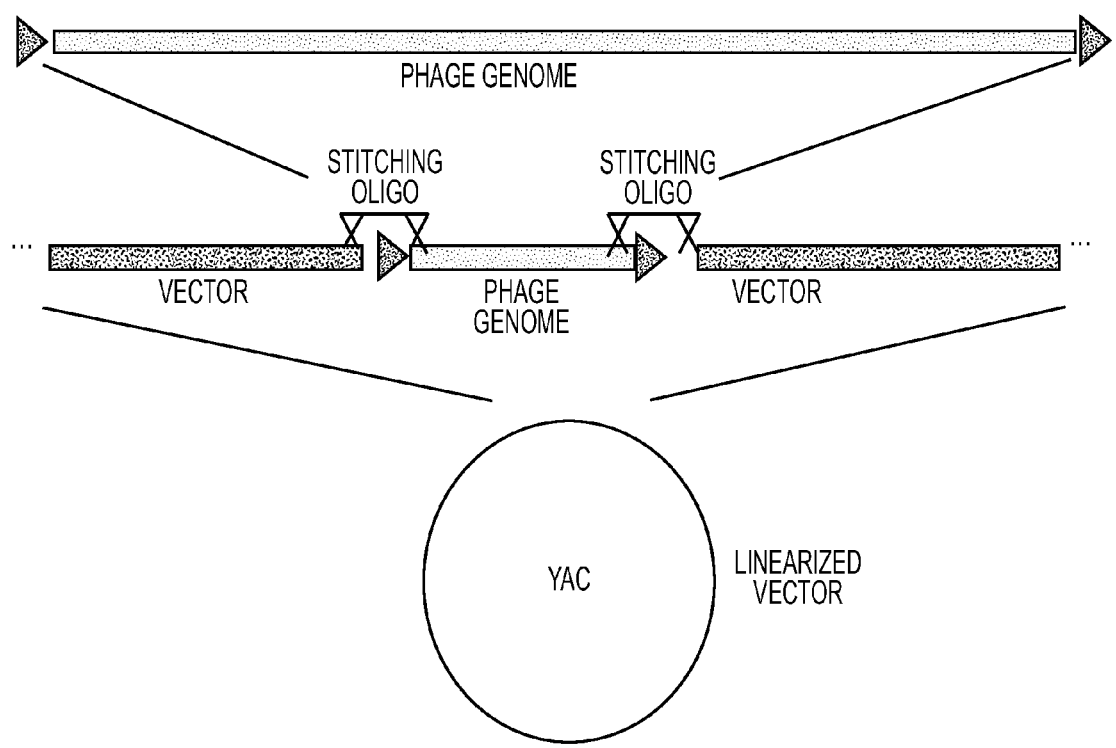
FIG. 2 shows a general strategy that may be used to capture a phage genome in a YAC vector. Stitching oligonucleotides that span the ends of the phage genome and sequences in the YAC are used to promote recombination between the phage genome and the YAC.

For capture of the A511 phage genome two different stitching oligonucleotide strategies were used (See FIG. 2). In the first, 80 bp double stranded stitching oligos bridging the ends of the phage genome and the YAC insertion sites were used. The first stitching oligo was

DBONO192

[SEQ ID NO: 36]
AAATAAAAAAAAATAAAACCAAAACCTGTAAAGCGCCCCGATCCACTA

GTTCTAGAGCGGCCGCCACCGCGGTGGAGCT and its complement.

The second stitching oligo was

DBONO199

[SEQ ID NO: 37]
TACGACTCACTATAGGGCGAATTGGGTACCGGGCCCCCCCAGCATTTTT

TTCACACGGTGTCAACTCAAAAGGCTTATAT and its complement.

In the second strategy stitching oligos of approximately 600 bases were constructed using a crossover PCR approach. Building the 600 bp fragments by PCR is a 2-step process. In the first step, the end regions of the phage and linearized vector are amplified. For example, DBONO186 and DBONO189 amplify the end of the A511 genome. DBONO189 adds 20 bp of homology to one linearized end of pRS415. DBONO188 and 187 amplify that end of pRS415, with DBONO188 adding 20 bp of homology to the end of A511. These PCR products were generated, purified using a QIAGEN PCR purification kit, and then diluted 1:10. 1 µl of each of these diluted products was used as template for the crossover PCR to generate the first 600 bp fragment.

The second 600 bp fragment was generated in a similar fashion. DBONO197 and DBONO194 amplify the other end of the A511 genome. DBONO97 adds 20 bp of homology to one linearized end of pRS415. DBONO193 and 198 amplify that end of pRS415, with DBONO198 adding 20 bp of homology to the end of A511. These PCR products were generated, purified using a QIAGEN PCR purification kit, and then diluted 1:10. 1 µl of each of these diluted products was used as template for the crossover PCR to generate the second 600 bp fragment.

The oligonucleotides used for PCR to generate the 600 bp fragments are:

DBONO186 [SEQ ID NO: 38]
GGTACCTTCGAGGCTAGCGG;

DBONO187 [SEQ ID NO: 39]
GCGCGTTGGCCGATTCATTA;

DBONO188 [SEQ ID NO: 40]
CAAAACCTGTAAAGCGCCCCGATCCACTAGTTCTAGAGCG;

DBONO189 [SEQ ID NO: 41]
CGCTCTAGAACTAGTGGATCGGGGCGCTTTACAGGTTTTG;

DBONO193 [SEQ ID NO: 42]
TAGGGCGCTGGCAAGTGTAG;

DBONO194 [SEQ ID NO: 43]
TCTTCTTTTTCATAAGATGCCTACACC;

DBONO197 [SEQ ID NO: 44]
ATTGGGTACCGGGCCCCCCCAGCATTTTTTTCACACGGTG;
and

DBONO198 [SEQ ID NO: 45]
CACCGTGTGAAAAAAATGCTGGGGGGCCCGGTACCCAAT.

Cotransforming yeast cells with linear pRS415, phage A511 genomic DNA purified as described above, and either the pair of 80 bp stitching oligos or the pair of 600 bp fragments was used to attempt to capture the A511 genome in the YAC. Out of 22 resulting clones analyzed using the 80 bp stitching oligos none contained the A511 genome. In contrast, in two experiments using different pRS415 DNA preps, 5 of 48 and 23 of 47 clones were found to contain the A511 genome. PCR was used to confirm the presence of intact termini of the A511 genome in the A511-YACs.

INFORMAL SEQUENCE LISTING

The following nucleotide sequences are referenced in this application:

| Sequence ID Number | Sequence |
|---|---|
| 1 | CCTAGTGTACCAGTATGATAGTACATCTCTATGTGTCCCTCCTCGCCGCAGTTAATTAAAGTCAGTGAGCGAGGAAGCGC |
| 2 | GAACGACCGAGCGCAGCGGCGGCCGCGCTGATACCGCCGCTCTCATAGTTCAAGAACCCAAAGTACCCCCCCCATAGCCC |
| 3 | CCTCATAAAGGCCAAGAAGGGCGGAAAGTCCAAATTGTAAACGGATTCACCACTCCAAGA |
| 4 | ATAATCATAGGTCCTCTGACACATAATTCGCCTCTCTGATTCAACGACAGGAGCACGATC |
| 5 | AAGAATTGATTGGCTCCAATTCTTGGAGTGGTGAATCCGTTTACAATTTGGACTTTCCGC |
| 6 | TCCTGGCCACGGGTGCGCATGATCGTGCTCCTGTCGTTGAATCAGAGAGGCGAATTATGT |
| 7 | AATTTACTCTTTACTCTTACAGATAACAGGACACTGAACGATGGAAGACGCCAAAAACAT |
| 8 | ATTCAGGCCACCTCATGATGACCTGTAAGAAAAGACTCTATTACAATTTGGACTTTCCGC |
| 9 | CTCACTAACGGGAACAACCTCAAACCATAGGAGACACATCATGGAAGACGCCAAAAACAT |
| 10 | TGTTTGCGTGCTTGATTGATTTACTCATGTTGTGCTCCTATTACAATTTGGACTTTCCGC |
| 11 | TTGTCTTTGGGTGTTACCTTGAGTGTCTCTCTGTGTCCCTCCTCGCCGCAGTTAATTAAAGTCAGTGAGCGAGGAAGCGC |
| 12 | CCCGAACGACCGAGCGCAGCGGCGGCCGCGCTGATACCGCCGCCGCGGCGTCTCACAGTGTACGGACCTAAAGTTCCCCCATAGGGGT |
| 13 | TAGAAATAATTTTGTTTAACTTTAAGAAGGAGATATACATATGGAAGACGCCAAAACAT |
| 14 | CCAAGGGGTTAACTAGTTACTCGAGTGCGGCCGCAAGCTTTTACAATTTGGACTTTCCGC |
| 15 | ACATTTTCTGGCGTCAGTCCACCAGCTAACATAAAATGTAAGCTTTCGGGGCTCTCTTGCCTTCCAACCCAGTCAGAAAT |
| 16 | AATTTACTCTTTACTCTTACAGATAACAGGACACTGAACGATGGTCTTCACACTCGAAGA |

-continued

| Sequence ID Number | Sequence |
|---|---|
| 17 | TTACGCCAGAATGCGTTCGCAC |
| 18 | AGTGACCGGCTGGCGGCTGTGCGAACGCATTCTGGCGTAACAGATTGTACTG AGAGTGCACC |
| 19 | ATTCAGGCCACCTCATGATGACCTGTAAGAAAAGACTCTACACACCGCATAGG GTAATAACTG |
| 20 | GAGTTCAACTTCTTTGGAGACATCTCAAGCACAGATTACAGATCCACTAGTTC TAGAGCGGCCGCCACCGCGGTGGAGCT |
| 21 | AGCGCGCGTAATACGACTCACTATAGGGCGAATTGGGTACATGACACCTGAA ATGTTCAGCCTTCTGAGTTCTGGTGTAT |
| 22 | TTCTATAAGCTGATGGCTTGGGTAAGAACTGCTTAATCCCAGGAAACAGGATC CAAATGGAAGACGCCAAAAACAT |
| 23 | CATAAAGAATATTAACACCATCTTAACAATCAGTCAATAATTACAATTTGGACTT TCCGC |
| 24 | TTTTAAGGGGAAACGAGATTTATTATTTGGAGAAAACATAATGGAAGACGCCA AAAACAT |
| 25 | TAACAGCATTTAAGTCCATTAAGCGCCTCCGCAAATAGAATTACAATTTGGACT TTCCGC |
| 26 | GATGACATCAAGTGTCTGTTCCCATAATAGGTGATTAACTATGGAAGACGCCA AAAACAT |
| 27 | TAGGTGTTCCATCAGACTCATAGCAGTGTTCAATTTTCATTTACAATTTGGACT TTCCGC |
| 28 | GGTTTTTAGATAGATTAAATTACACATCAACGGGGAGGGAATGGAAGACGCCA AAAACAT |
| 29 | GGGCTTACTTTACAGACTTTTAAGCCCCATGTAAAGCACTTTACAATTTGGACT TTCCGC |
| 30 | CTCCCCACTAAATAAAACCCTTAAACTAGGAGATTCTAAAATGGAAGACGCCA AAAACAT |
| 31 | CTGTTAGGGTATCTGGGGCTATTTAGCCCCGCTGCGTCGATTACAATTTGGAC TTTCCGC |
| 32 | GCCAAACTGTCTTGAAAACAGTTGCCACTGTAGAGATACGATGGAAGACGCC AAAAACAT |
| 33 | ACAACAAGCGGTAATAACCTTAGAAGCCCTCTAAAAAGACTTACAATTTGGAC TTTCCGC |
| 34 | GATGACATCAAGTGTCTGTTCCCATAATAGGTGATTAACTATGGAAGACGCCA AAAACAT |
| 35 | TAGGTGTTCCATCAGACTCATAGCAGTGTTCAATTTTCATTTACAATTTGGACT TTCCGC |
| 36 | AAATAAAAAAAAATAAAACCAAAACCTGTAAAGCGCCCCGATCCACTAGTTC TAGAGCGGCCGCCACCGCGGTGGAGCT |
| 37 | TACGACTCACTATAGGGCGAATTGGGTACCGGGCCCCCCCAGCATTTTTTC ACACGGTGTCAACTCAAAAGGCTTATAT |
| 38 | GGTACCTTCGAGGCTAGCGG |
| 39 | GCGCGTTGGCCGATTCATTA |
| 40 | CAAAACCTGTAAAGCGCCCCGATCCACTAGTTCTAGAGCG |
| 41 | CGCTCTAGAACTAGTGGATCGGGGCGCTTTACAGGTTTTG |
| 42 | TAGGGCGCTGGCAAGTGTAG |
| 43 | TCTTCTTTTTCATAAGATGCCTACACC |

| Sequence ID Number | Sequence |
|---|---|
| 44 | ATTGGGTACCGGGCCCCCCAGCATTTTTTTCACACGGTG |
| 45 | CACCGTGTGAAAAAAATGCTGGGGGGCCCGGTACCCAAT |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of making a recombinant phage genome, comprising:
   (a) selecting a starting phage genome and a eukaryotic vector;
   (b) selecting a stitching oligonucleotide or oligonucleotide duplex for recombination with the starting phage genome and the eukaryotic vector comprising:
      (i) detecting an imperfect oligo repeat at an end of the starting phage genome, and selecting a stitching oligonucleotide comprising a sequence from the ends of the starting phage genome and a sequence flanking the double strand break in the eukaryotic vector;
      (ii) detecting a perfect oligo repeat at an end of the starting phage genome and selecting a oligonucleotide duplex comprising a sequence homologous to the starting phage genome and a sequence homologous to the eukaryotic vector;
   (c) introducing the starting phage genome and the eukaryotic vector of step (a), and the stitching oligonucleotide or the oligonucleotide duplex of step (b) into a plurality of eukaryotic vector host cells that are not phage host cells;
   (d) selecting a vector host cell comprising a recombinant vector comprising an intact starting phage genome as a result of insertion of the starting phage genome into the vector; and
   (e) inserting a heterologous nucleic acid sequence comprising an open reading frame encoding a screenable marker into the intact starting phage genome to provide a recombinant intact phage genome, wherein the screenable marker is operatively linked to a regulatory control sequence.

2. The method of claim 1, wherein c) comprises co-transforming the starting phage genome and the vector into a plurality of vector host cells, under conditions that allow insertion of the starting phage genome into the vector.

3. The method of claim 1, wherein c) comprises transforming the starting phage genome into a plurality of vector host cells comprising the vector, under conditions that allow insertion of the starting phage genome into the vector.

4. The method of claim 1, wherein the vector is a yeast artificial chromosome (YAC).

5. The method of claim 1, wherein the heterologous nucleic acid sequence is inserted into the intact starting phage genome in vivo.

6. The method of claim 1, wherein the heterologous nucleic acid sequence is inserted into the intact starting phage genome in vitro.

7. The method of claim 1, further comprising f) transforming the recombinant intact phage genome into competent phage host cells.

8. The method of claim 7, further comprising g) producing and recovering recombinant phage particles comprising the recombinant intact phage genome from said competent phage host cells.

* * * * *

SEQUENCE LISTING

```
<160> NUMBER OF SEQ ID NOS: 46

<210> SEQ ID NO 1
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cctagtgtac cagtatgata gtacatctct atgtgtccct cctcgccgca gttaattaaa      60
gtcagtgagc gaggaagcgc                                                  80

<210> SEQ ID NO 2
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gaacgaccga gcgcagcggc ggccgcgctg ataccgccgc tctcatagtt caagaaccca      60 aagtacccccc cccatagccc                                                 80

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cctcataaag gccaagaagg gcggaaagtc caaattgtaa acggattcac cactccaaga      60

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ataatcatag gtcctctgac acataattcg cctctctgat tcaacgacag gagcacgatc      60
```

```
<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aagaattgat tggctccaat tcttggagtg gtgaatccgt ttacaatttg gactttccgc    60

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcctggccac gggtgcgcat gatcgtgctc ctgtcgttga atcagagagg cgaattatgt    60

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aatttactct ttactcttac agataacagg acactgaacg atggaagacg ccaaaaacat    60

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
attcaggcca cctcatgatg acctgtaaga aaagactcta ttacaatttg gactttccgc    60

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctcactaacg ggaacaacct caaaccatag gagacacatc atggaagacg ccaaaaacat    60

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgtttgcgtg cttgattgat ttactcatgt tgtgctccta ttacaatttg gactttccgc    60
```

```
<210> SEQ ID NO 11
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttgtctttgg gtgttacctt gagtgtctct ctgtgtccct cctcgccgca gttaattaaa    60
gtcagtgagc gaggaagcgc                                                80

<210> SEQ ID NO 12
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cccgaacgac cgagcgcagc ggcggccgcg ctgataccgc cgccgccggc gtctcacagt    60
gtacggacct aaagttcccc cataggggt                                      90

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tagaaataat tttgtttaac tttaagaagg agatatacat atggaagacg ccaaaaacat    60

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccaaggggtt aactagttac tcgagtgcgg ccgcaagctt ttacaatttg gactttccgc    60

<210> SEQ ID NO 15
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
acattttctg gcgtcagtcc accagctaac ataaaatgta agctttcggg gctctcttgc    60
cttccaaccc agtcagaaat                                                80

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 16
aatttactct ttactcttac agataacagg acactgaacg atggtcttca cactcgaaga    60

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttacgccaga atgcgttcgc ac    22

<210> SEQ ID NO 18
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agtgaccggc tggcggctgt gcgaacgcat tctggcgtaa cagattgtac tgagagtgca    60
cc    62

<210> SEQ ID NO 19
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
attcaggcca cctcatgatg acctgtaaga aaagactcta cacaccgcat agggtaataa    60
ctg    63

<210> SEQ ID NO 20
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gagttcaact tctttggaga catctcaagc acagattaca gatccactag ttctagagcg    60
gccgccaccg cggtggagct    80

<210> SEQ ID NO 21
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agcgcgcgta atacgactca ctatagggcg aattgggtac atgacacctg aaatgttcag    60
ccttctgagt tctggtgtat    80

<210> SEQ ID NO 22

```
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttctataagc tgatggcttg ggtaagaact gcttaatccc aggaaacagg atccaaatgg      60
aagacgccaa aaacat                                                     76

<210> SEQ ID NO 23
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cataaagaat attaacacca tcttaacaat cagtcaataa ttacaatttg gactttccgc      60

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ttttaagggg aaacgagatt tattatttgg agaaaacata atggaagacg ccaaaaacat      60

<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
taacagcatt taagtccatt aagcgcctcc gcaaatagaa ttacaatttg gactttccgc      60

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gatgacatca agtgtctgtt cccataatag gtgattaact atggaagacg ccaaaaacat      60

<210> SEQ ID NO 27
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
taggtgttcc atcagactca tagcagtgtt caattttcat ttacaatttg gactttccgc      60
```

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
ggtttttaga tagattaaat tacacatcaa cggggaggga atggaagacg ccaaaaacat    60

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
gggcttactt tacagacttt taagccccat gtaaagcact ttacaatttg gactttccgc    60

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
ctccccacta aataaaaccc ttaaactagg agattctaaa atggaagacg ccaaaaacat    60

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
ctgttagggt atctggggct atttagcccc gctgcgtcga ttacaatttg gactttccgc    60

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
gccaaactgt cttgaaaaca gttgccactg tagagatacg atggaagacg ccaaaaacat    60

<210> SEQ ID NO 33
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
acaacaagcg gtaataacct tagaagccct ctaaaaagac ttacaatttg gactttccgc    60

<210> SEQ ID NO 34

<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gatgacatca agtgtctgtt cccataatag gtgattaact atggaagacg ccaaaaacat    60

<210> SEQ ID NO 35
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
taggtgttcc atcagactca tagcagtgtt caattttcat ttacaatttg gactttccgc    60

<210> SEQ ID NO 36
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aaataaaaaa aaaataaaac caaaacctgt aaagcgcccc gatccactag ttctagagcg    60
gccgccaccg cggtggagct                                                80

<210> SEQ ID NO 37
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tacgactcac tatagggcga attgggtacc gggcccccccc agcatttttt tcacacggtg    60
tcaactcaaa aggcttatat                                                80

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ggtaccttcg aggctagcgg                                                20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcgcgttggc cgattcatta                                                20

<210> SEQ ID NO 40
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
caaaacctgt aaagcgcccc gatccactag ttctagagcg                              40

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cgctctagaa ctagtggatc ggggcgcttt acaggttttg                              40

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tagggcgctg gcaagtgtag                                                    20

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tcttcttttt cataagatgc ctacacc                                            27

<210> SEQ ID NO 44
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
attgggtacc gggccccccc agcatttttt tcacacggtg                              40

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
caccgtgtga aaaaaatgct ggggggggcc ggtacccaat                              40

```
<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 46

His His His His His His
1               5
```